(12) United States Patent
Oleinikov

(10) Patent No.: US 7,323,320 B2
(45) Date of Patent: *Jan. 29, 2008

(54) MICROARRAY SYNTHESIS AND ASSEMBLY OF GENE-LENGTH POLYNUCLEOTIDES

(75) Inventor: Andrew V. Oleinikov, Mill Creek, WA (US)

(73) Assignee: Combimatrix Corporation, Mukilteo, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/201,629

(22) Filed: Aug. 10, 2005

(65) Prior Publication Data

US 2005/0287585 A1 Dec. 29, 2005

Related U.S. Application Data

(63) Continuation of application No. 10/243,367, filed on Sep. 12, 2002.

(51) Int. Cl.
C12P 19/34 (2006.01)
(52) U.S. Cl. .................. 435/91.5; 435/6; 435/41; 435/91.1; 435/91.2
(58) Field of Classification Search ............... 435/91.5, 435/6, 41, 91.1, 91.2
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 4,999,294 A | 3/1991 | Looney et al. | |
| 5,082,767 A | 1/1992 | Hatfield et al. | |
| 5,093,251 A | 3/1992 | Richards et al. | |
| 5,096,825 A | 3/1992 | Barr et al. | |
| 5,104,789 A | 4/1992 | Permar et al. | |
| 5,132,215 A | 7/1992 | Jayarama et al. | |
| 5,143,854 A | 9/1992 | Pirrung et al. | |
| 5,356,802 A | 10/1994 | Chandrasegaran | |
| 5,395,750 A | 3/1995 | Dillon et al. | |
| 5,405,783 A | 4/1995 | Pirrung et al. | |
| 5,424,186 A | 6/1995 | Fodor et al. | |
| 5,436,150 A | 7/1995 | Chandrasegaran | |
| 5,436,327 A | 7/1995 | Southern et al. | |
| 5,459,039 A | 10/1995 | Modrich et al. | |
| 5,498,531 A | 3/1996 | Jarrell | |
| 5,556,750 A | 9/1996 | Modrich et al. | |
| 5,605,793 A | 2/1997 | Stemmer | |
| 5,661,028 A | 8/1997 | Foote | |
| 5,667,667 A | 9/1997 | Southern | |
| 5,679,522 A | 10/1997 | Modrich et al. | |
| 5,695,940 A | 12/1997 | Drmanac et al. | |
| 5,700,637 A | 12/1997 | Southern | |
| 5,702,894 A | 12/1997 | Modrich et al. | |
| 5,750,335 A | 5/1998 | Gifford | |
| 5,766,550 A | 6/1998 | Kaplan et al. | |
| 5,780,272 A | 7/1998 | Jarrell | |
| 5,834,233 A | 11/1998 | Molin et al. | |
| 5,834,252 A | 11/1998 | Stemmer et al. | |
| 5,858,754 A | 1/1999 | Modrich et al. | |
| 5,861,482 A | 1/1999 | Modrich et al. | |
| 5,912,129 A | 6/1999 | Vinayagamoorthy et al. | |
| 5,916,794 A | 6/1999 | Chandrasegaran | |
| 5,922,539 A | 7/1999 | Modrich et al. | |
| 5,928,905 A | 7/1999 | Stemmer et al. | |
| 5,942,609 A | 8/1999 | Hunkapiller et al. | |
| 5,953,469 A | 9/1999 | Zhou | |
| 6,008,031 A | 12/1999 | Modrich et al. | |
| 6,013,440 A * | 1/2000 | Lipshutz et al. | ............... 435/6 |
| 6,017,696 A | 1/2000 | Heller et al. | |
| 6,027,877 A | 2/2000 | Wagner, Jr. | |
| 6,027,910 A | 2/2000 | Klis et al. | |
| 6,093,302 A | 7/2000 | Montgomery | |
| 6,110,668 A | 8/2000 | Strizhov et al. | |
| 6,114,147 A | 9/2000 | Frenken et al. | |
| 6,136,568 A | 10/2000 | Hiatt et al. | |
| 6,143,527 A | 11/2000 | Pachuk et al. | |
| 6,150,102 A | 11/2000 | Jarrell | |
| 6,150,141 A | 11/2000 | Jarrell | |
| 6,165,793 A | 12/2000 | Stemmer | |
| 6,261,797 B1 | 7/2001 | Sorge et al. | |

(Continued)

FOREIGN PATENT DOCUMENTS

EP     0259160 A2     3/1988

(Continued)

OTHER PUBLICATIONS

Stemmer, W.P.C. DNA Shuffling by Random Fragmentation and Reassembly: In Vitro Recombination for Molecular Evolution. Proc. Natl. Acad. Sci. USA (Oct. 1994), vol. 91, pp. 10747-10751.*
Oleinikov, A.V. et al. Self-Assembling Protein Arrays Using Electronic Semiconductor Microchips and In Vitro Translation. Journal of Proteome Research (2003), vol. 2, pp. 313-319, (published on Web Apr. 5, 2003).*
Oleinikov, A.V. et al. RNA Interference by Mixtures of siRNAs Prepared Using Custom Oligonucleotide Arrays. Nucleic Acids Res. (2005), vol. 33, No. 10, pp. e92, (published online Jul. 7, 2005).*
Au, L.C., et al., "Gene Synthesis by a LCR-Based Approach: High-Level Production of Leptin-L54 Using Synthetic Gene in *Escherichia coli*," Biochemical and Biophysical Research Communications, 248:200-203 (1998).

(Continued)

*Primary Examiner*—Mark L. Shibuya
(74) *Attorney, Agent, or Firm*—Ropes & Gray LLP

(57) ABSTRACT

There is disclosed a process for in vitro synthesis and assembly of long, gene-length polynucleotides based upon assembly of multiple shorter oligonucleotides synthesized in situ on a microarray platform. Specifically, there is disclosed a process for in situ synthesis of oligonucleotide fragments on a solid phase microarray platform and subsequent, "on device" assembly of larger polynucleotides composed of a plurality of shorter oligonucleotide fragments.

23 Claims, 14 Drawing Sheets

U.S. PATENT DOCUMENTS

| | | |
|---|---|---|
| 6,271,957 B1 | 8/2001 | Quate et al. |
| 6,277,632 B1 | 8/2001 | Harney |
| 6,280,595 B1 | 8/2001 | Montgomery |
| 6,284,463 B1 | 9/2001 | Hasebe et al. |
| 6,287,825 B1 | 9/2001 | Weissman et al. |
| 6,287,861 B1 | 9/2001 | Stemmer et al. |
| 6,291,242 B1 | 9/2001 | Stemmer et al. |
| 6,315,958 B1 | 11/2001 | Singh-Gasson et al. |
| 6,322,971 B1 | 11/2001 | Chetverin et al. |
| 6,326,489 B1 | 12/2001 | Church et al. |
| 6,333,153 B1 | 12/2001 | Fishel et al. |
| 6,346,399 B1 | 2/2002 | Weissman et al. |
| 6,355,412 B1 | 3/2002 | Stewart et al. |
| 6,358,712 B1 | 3/2002 | Jarrell et al. |
| 6,365,355 B1 | 4/2002 | McCutchen-Maloney |
| 6,372,429 B1 | 4/2002 | Sharon |
| 6,372,434 B1 | 4/2002 | Weissman et al. |
| 6,375,903 B1 | 4/2002 | Cerrina et al. |
| 6,376,246 B1 | 4/2002 | Crameri et al. |
| 6,406,847 B1 | 6/2002 | Cox et al. |
| 6,426,184 B1 | 7/2002 | Gao et al. |
| 6,444,111 B1 | 9/2002 | Montgomery |
| 6,444,175 B1 | 9/2002 | Singh-Gasson et al. |
| 6,472,184 B1 | 10/2002 | Hegemann |
| 6,480,324 B2 | 11/2002 | Quate et al. |
| 6,489,146 B2 | 12/2002 | Stemmer et al. |
| 6,495,318 B2 | 12/2002 | Harney |
| 6,509,156 B1 | 1/2003 | Stewart et al. |
| 6,521,427 B1 | 2/2003 | Evans |
| 6,586,211 B1 | 7/2003 | Stahler et al. |
| 6,593,111 B2 | 7/2003 | Baric et al. |
| 6,650,822 B1 | 11/2003 | Zhou |
| 6,664,112 B2 | 12/2003 | Mulligan et al. |
| 6,670,127 B2 | 12/2003 | Evans |
| 6,696,587 B2 | 2/2004 | Jenkner |
| 6,897,025 B2 | 5/2005 | Cox et al. |
| 6,921,636 B1 | 7/2005 | Brennan |
| 6,921,818 B2 | 7/2005 | Sproat |
| 6,936,470 B2 | 8/2005 | Liang et al. |
| 6,946,296 B2 | 9/2005 | Patten et al. |
| 6,955,883 B2 | 10/2005 | Margus et al. |
| 6,969,847 B2 | 11/2005 | Davis et al. |
| 2001/0031483 A1 | 10/2001 | Sorge et al. |
| 2001/0049125 A1 | 12/2001 | Stemmer et al. |
| 2002/0012616 A1 | 1/2002 | Zhou et al. |
| 2002/0058275 A1 | 5/2002 | Fishel et al. |
| 2002/0081582 A1 | 6/2002 | Gao et al. |
| 2002/0133359 A1 | 9/2002 | Wagner, Jr. et al. |
| 2003/0224521 A1 | 12/2002 | Court et al. |
| 2003/0017552 A1 | 1/2003 | Jarrell et al. |
| 2003/0044980 A1 | 3/2003 | Mancebo et al. |
| 2003/0050437 A1 | 3/2003 | Montgomery |
| 2003/0050438 A1 | 3/2003 | Montgomery |
| 2003/0068633 A1 | 4/2003 | Belshaw et al. |
| 2003/0068643 A1 | 4/2003 | Brennan et al. |
| 2003/0087298 A1 | 5/2003 | Green et al. |
| 2003/0091476 A1 | 5/2003 | Zhou et al. |
| 2003/0099952 A1 | 5/2003 | Green et al. |
| 2004/0092016 A1 | 5/2003 | Court et al. |
| 2003/0118485 A1 | 6/2003 | Singh-Gasson et al. |
| 2003/0118486 A1 | 6/2003 | Zhou et al. |
| 2003/0120035 A1 | 6/2003 | Gao et al. |
| 2003/0134807 A1 | 7/2003 | Hardin et al. |
| 2003/0140255 A1 | 7/2003 | Ricchetti et al. |
| 2003/0143550 A1 | 7/2003 | Green et al. |
| 2003/0143724 A1 | 7/2003 | Cerrina et al. |
| 2003/0171325 A1 | 9/2003 | Gascoyne et al. |
| 2003/0186226 A1 | 10/2003 | Brennan et al. |
| 2003/0186233 A1 | 10/2003 | Chesnut et al. |
| 2003/0198948 A1 | 10/2003 | Stahler et al. |
| 2003/0215856 A1 | 11/2003 | Church et al. |
| 2004/0005673 A1 | 1/2004 | Jarrell et al. |
| 2004/0009520 A1 | 1/2004 | Albert et al. |
| 2004/0014083 A1 | 1/2004 | Yuan et al. |
| 2004/0096891 A1 | 5/2004 | Bennett |
| 2004/0101444 A1 | 5/2004 | Sommers et al. |
| 2004/0101894 A1 | 5/2004 | Albert et al. |
| 2004/0101949 A1 | 5/2004 | Green et al. |
| 2004/0110211 A1 | 6/2004 | McCormick et al. |
| 2004/0110212 A1 | 6/2004 | McCormick et al. |
| 2004/0126757 A1 | 7/2004 | Cerrina |
| 2004/0132029 A1 | 7/2004 | Sussman et al. |
| 2004/0166567 A1 | 8/2004 | Santi et al. |
| 2004/0224336 A1 | 11/2004 | Wagner |
| 2004/0259146 A1 | 12/2004 | Friend et al. |
| 2004/0259256 A1 | 12/2004 | Monahan et al. |
| 2005/0053979 A1 | 3/2005 | Livak et al. |
| 2005/0053997 A1 | 3/2005 | Evans |
| 2005/0079618 A1 | 4/2005 | Court et al. |
| 2005/0106606 A1 | 5/2005 | Parker et al. |
| 2005/0112631 A1 | 5/2005 | Piepenburg et al. |
| 2005/0118628 A1 | 6/2005 | Evans |
| 2005/0196760 A1 | 9/2005 | Pernov et al. |
| 2005/0196865 A1 | 9/2005 | Frazer |
| 2005/0208503 A1 | 9/2005 | Yowanto et al. |
| 2005/0208536 A1 | 9/2005 | Schultz et al. |
| 2005/0221340 A1 | 10/2005 | Evans |
| 2005/0227235 A1 | 10/2005 | Carr et al. |
| 2005/0240352 A1 | 10/2005 | Liang |
| 2005/0255477 A1 | 11/2005 | Carr et al. |
| 2006/0008833 A1 | 1/2006 | Jacobson |
| 2006/0024733 A1 | 2/2006 | Wong et al. |

FOREIGN PATENT DOCUMENTS

| | | |
|---|---|---|
| EP | 0385410 A2 | 9/1990 |
| WO | WO-9000626 | 1/1990 |
| WO | WO-96/27025 | 9/1996 |
| WO | WO-96/33207 | 10/1996 |
| WO | WO-99/41007 | 8/1999 |
| WO | WO-01/34847 | 5/2001 |
| WO | WO-02/02227 | 1/2002 |
| WO | WO-02/04597 | 1/2002 |
| WO | WO-02/04680 | 1/2002 |
| WO | WO-02/44425 | 6/2002 |
| WO | WO-02/072791 | 9/2002 |
| WO | WO-02/081490 | 10/2002 |
| WO | WO-02/095073 | 11/2002 |
| WO | WO-02103446 A2 | 12/2002 |
| WO | WO-03/040410 | 5/2003 |
| WO | WO-03/046223 | 6/2003 |
| WO | WO-03/054232 | 7/2003 |
| WO | WO-03/064026 | 8/2003 |
| WO | WO-03/064027 | 8/2003 |
| WO | WO-03/064699 | 8/2003 |
| WO | WO-03/065038 | 8/2003 |
| WO | WO-03/066212 | 8/2003 |
| WO | WO-03/072832 | 9/2003 |
| WO | WO-03/085094 | 10/2003 |
| WO | WO-03/100012 | 12/2003 |
| WO | WO-2004/024886 A2 | 3/2004 |
| WO | WO-2004/029586 | 4/2004 |
| WO | WO-2004/031351 | 4/2004 |
| WO | WO-2004/031399 | 4/2004 |
| WO | WO-2004/039953 | 5/2004 |
| WO | WO-2005/089110 | 9/2005 |

OTHER PUBLICATIONS

Chakrabarti, R. and Schutt, C. "Novel Sulfoxides Facilitate GC-Rich Template Amplification" BioTechniques 32(4):866-873 (2002).

Dillon, P. and Rosen, C. "A Rapid Method for the Construction of Synthetic Genes Using the Polymerase Chain Reaction" Biofeedback 9(3):299-300 (1990).

Higuchi, R., et al., "A general method of in vitro preparation and specific mutagenesis of DNA fragments: study of protein and DNA interactions," Nucleic Acids Research, 16(15):7351-7367 (1988).

Hoover, D. and Lubkowski, J. "DNAWorks: an automated method for designing oligonucleotides for PCR-based gene synethesis" Nucl. Acids. Res. 30(10):e43 (2002).

Mullis, K. et al. "Specific Enzymatic Amplification of DNA In Vitro: The Polymerase Chain Reaction" Cold Spring Harbor Symposia on Quantitative Biology, vol. L1 (1986).

Pachuk, C.J., et al., "Chain reaction cloning: a one-step method for directional ligation of multiple DNA fragments," Gene, 243:19-25 (2000).

Pan, X., et al., "An approach for global scanning of single nucleotide variations," PNAS, 99(14):9346-9351 (2002).

Smith, J. and Modrich, P. "Removal of polymerase-produced mutant sequences from PCR products" PNAS 94:6847-6850 (1997).

Stemmer, W.P.C. et al. "Single-step assembly of a gene and entire plasmid from large numbers of oligodeoxyribonucleotides" Gene 164:49-53 (1995).

Cello, J., et al., "Chemical Synthesis of Poliovirus cDNA: Generation of Infectious Virus in the Absence of Natural Template," Science, 297:1016-1018 (2002).

Cleary, M.A., et al., "Production of complex nucleic acid libraries using highly parallel in situ oligonucleotide synthesis," Nature Methods, 1(3):241-248 (2004).

Dahl, F., et al., "Circle-to-circle amplification for precise and sensitive DNA analysis," PNAS, 101(13):4548-4553 (2004).

Dalgleish, R., "The Polymerase Chain Reaction (PCR)," PCR explanation, Univ. of Leicester UK.

Dirks, R.M., et al., "Triggered amplification by hybridization chain reaction," PNAS, 101(43):15275-15278 (2004).

Donahue, W.F., et al., "Rapid gene cloning using terminator primers and modular vectors," 30(18):e95 (6 pages) (2002).

Ferber, D., "Microbes Made to Order," Science, 303:158-161 (2004).

Ferretti, L., et al., "Total synthesis of a gene for bovine rhodopsin," PNAS, 83:599-603 (1986).

Gryaznov, S.M., et al., "Enhancement of selectivity in recognition of nucleic acids via chemical autoligation," Nucleic Acids Research, 22(12):2366-2369 (1994).

Gupta, N.K., et al., "Studies on Polynucleotides, LXXXVIII. Enzymatic Joining of Chemical Synthesized Segments Corresponding to the Gene for Alanine-tRNA," PNAS, 60(4):1338-1344 (1968).

Hasan, A., et al., "Photolabile Protecting Groups for Nucleosides: Synthesis and Photodeprotection Rates," Tetrahedron, 53(12):4247-4264 (1997).

Hasty, J., et al., "Engineered gene circuits," Nature, 420:224-230 (2002).

Hecker, K.H., et al., "Error Analysis of Chemically Synthesized Polynucleotides," BioTechniques, 24:256-260 (1998).

Heller, M.J., "DNA Microarray Technology: Devices, Systems and Applications," Annu. Rev. Biomed. Eng., 4:129-153 (2002).

Henegariu, O. et al., "Multiplex PCR: Critical Parameters and Step-by-Step Protocol," BioTechniques, 23(3):504-511 (1997).

Hingorani, M.M., "DNA Polymerase Structure and Mechanisms of Action," Current Organic Chemistry, 4:887:913 (2000).

Hogrefe, H.H., et al., "Archaeal dUTPase enhances PCR amplifications with archael DNA polymerases by preventing dUTP incorporation," PNAS, 99(2):596-601 (2002).

Hoover, D.M., et al., "DNAWorks: an automated method for designing oligonucleotides for PCR-based gene synthesis," Nucleic Acids Research, 30(10):e43 (7 pages) (2002).

Housby, J.N., et al., "Fidelity of DNA ligation: a novel experimental approach based on the polymerisation of libraries of oligonucleotides," Nucleic Acids Research, 26(18):4259-4266 (1998).

Ihle, O., et al., "Efficient purification of DNA fragments using a protein binding membrane," Nucleic Acids Research, 28(16):e76 (6 pages) (2000).

Itaya, M., et al., "Experimental surgery to create subgenomes of Bacillus subtilis 168," PNAS, 94:5378-5382 (1997).

James, K.D., et al., "The Fidelity of Template-Directed Oligonucleotide Ligation and the Inevitability of Polymerase Function," Origins of Life and Evolution of the Biosphere, 29:375-390 (1999).

Khorana, H.G., et al., "Studies on Polynucleotides: Total Synthesis of the Structural Gene for an Alanine Transfer Ribonucleic Acid from Yeast," J. Mol. Biol., 72:209-217 (1972).

Khorana, H.G., "Total Synthesis of a Gene," Science, 203:614-625 (1979).

Kim, C., et al., "Biological lithography: Improvements in DNA synthesis methods," J. Vac. Sci. Technol. B, 22(6):3163-3167 (2004).

Kleppe, K., et al., "Studies on Polynucleotides: Repair Replication of Short Synthetic DNA's as catalyzed by DNA Polymerases," J. Mol. Biol., 56:341-361 (1971).

Kneidinger, B., et al., "Scaling Up the Ligase Chain Reaction-Based Approach to Gene Synthesis," BioTechniques, 30:249-252 (2001).

Kodumal, S.J., et al., "Total synthesis of long DNA sequences: Synthesis of a continguous 32-kb polyketide synthase gene cluster," PNAS, 101(44):15573-15578 (2004).

Kuzminov, A., "Recombinatorial Repair of DNA Damage in Escherichia coli and Bacteriophage λ," Microbiology and Molecular Biology Reviews, 63(4):751-813 (1999).

Laski, F.A., et al., "An amber suppressor tRNA gene derived by site-specific mutagenesis: Cloning and function in mammalian cells," PNAS, 79:5813-5817 (1982).

Lin, Y., et al., "The use of synthetic genes for the expression of a ciliate proteins in heterologous systems," Gene, 288:85-94 (2002).

Mandecki, W., et al., "Fokl method of gene synthesis," Gene, 68:101-107 (1988).

Mitra, R.D., et al., "Fluorescent in situ sequencing on polymerase colonies," Analytical Biochemistry, 320:55-65 (2003).

Mullis, K., et al., "Specific Enzymatic Amplification of DNA in Vitro: The Polymerase Chain Reaction," Cold Spring Harbor Symposia on Quantitative Biology, vol. LI (1986).

Poteete, A.R., et al., "Genetic Requirements of Phage λ Red-Mediated Gene Replacement in Escherichia coli K-12," J. Bacteriology, 182(8):2336-2340 (2000).

Qiagen Miltiplex PCR Handbook, Jul. 2004, www.qiagen.com.

Ren, Q., et al., "Comparative Analyses of Fundamental Differences in Membrane Transport Capabilities in Prokaryotes and Eukaryotes," PLoS Computational Biology, 1(3):0190-0201 (2005).

Richmond, K.E., et al., Amplification and assembly of chip-eluted DNA (AACED): a method for high-throughput gene synthesis, Nucleic Acids Research, 32(17):5011-5018 (2004).

Rouillard, J.M., et al., "Gene2oligo: oligonucleotide design for in vitro gene synthesis," Nucleic Acids Resarch, 32:W176-W180 (2004).

Schwarz, K., et al., "Improved yields of long PCR products using gene 32 protein," Nucleic Acids Research, 18(4):1079 (1989).

Sgaramella, V., et al., "Studies on Polynucleotides, C. A Novel Joining Reaction Catalyzed by the T4-Polynucleotide Ligase," PNAS, 67(3):1468-1475 (1970).

Shabarova, Z.A., et al., "Chemical ligation of DNA: the first non-enzymatic assembly of a biologically active gene," Nucleic Acids Research, 19(15):4247-4251 (1991).

Shigemori, Y., et al., "Multiplex PCR: use of heat-stable Thermus thermophilus RecA protein to minimize non-specific PCR products," Nucleic Acids Research, 33(14):e126 (9 pages) (2005).

Smith, J., et al., "A detailed study of the substrate specificity of a chimeric restriction enzyme," Nucleic Acids Research, 27(2):674-681 (1999).

Sokolova, N.I., et al., "Chemical reactions within DNA duplexes, Cyanogen bromide as an effective oligodeoxyribonucleotie coupling agent," FEBS Letters, 232(1):153-155 (1988).

Stemmer, W.P.C., et al., "Single-step assembly of a gene and entire plasmid from large numbers of oligodeoxyribonucleotides," Gene, 164:49-53 (1995).

Taud, A.H., "The General and Logical Theory of Automata," John von Neumann, vol. 5, 288-326.

Tian, J., et al., "Accurate multiplex gene synthesis from programmable DNA microchips," Nature, 432:1050-1054 (2004).

Tindall, K.R., et al., "Fidelity of DNA Synthesis by the *Thermus aquaticus* DNA Polymerase," Biochemistry, 27(16):6008-6013 (1988).

Tong, J., et al., "Biochemical properties of a high fidelity DNA ligase from Thermus species AK16D," Nucleic Acids Research, 27(3):788-794 (1999).

Tsuge, K., et al., "One step assembly of multiple DNA fragments with a designed order and orientation in *Bacillus subtilis* plasmid," Nucleic Acids Research, 31(21):e133 (8 pages) (2003).

Withers-Martinez, C., et al., "PCR-based gene synthesis as an efficient approach for expression of the A+T-rich malaria genome," Protein Engineering, 12(12):1113-1120 (1999).

Xiong, A.S., et al., "A simple, rapid, high-fidelity and cost-effective PCR-based two-step DNA synthesis method for long gene sequences," Nucleic Acids Research, 32(12):e98 (10 pages) (2004).

Xu, Y., et al., "High sequence fidelity in a non-enzymatic DNA autoligation reaction," Nucleic Acids Research, 27(3):875-881 (1999).

Xu, Y., et al., "Nonenzymatic autoligation in direct three-color detection of RNA and DNA point mutations," Nature Biotechnology, 19:148-152 (2001).

Yanez, J., et al., "Combinatorial codon-based amino acid substitutions," Nucleic Acids Research, 32(20):e158 (10 pages) (2004).

Young, L., et al., "Two-step total gene synthesis method," Nucleic Acids Research, 32(7):e59 (6 pages) (2004).

Yu, D., et al., "An efficient recombination system for chromosome engineering in *Escherichia coli*," PNAS, 97(11):5978-5983 (2000).

Zhang, Y., et al., "Phage annealing proteins promote oligonucleotide-directed mutagenesis in *Escherichia coli* and mouse ES cells," BMC Molecular Biology, 4:1-14 (2003).

Zhou, X., et al., "Microfluidic PicoArray synthesis of oligodeoxynucleotides and simultaneous assembling of multiple DNA sequences," Nucleic Acids Research, 32(18):5409-5417 (2004).

Zimmer, C., Tinker, Tailor: Can Venter Stitch Together a Genome From Scratch?, Science, 299:1006-1007 (2003).

Mandecki, W., "Oligonucleotide-directed double-strand break repair in plasmids of *Escherichia coli*: A method for site-specific mutagenesis," Proc. Natl. Acad. Sci. USA, 83:7177-7181 (1986).

Chetverin et al., "Sequencing of Pools of Nucleic Acids on Olignucleotide Arrays," Biosystems, 30:215-231 (1993).

Horton, et al., "Engineering Hybrid Genes Without the Use of Restriction Enzymes: Gene Splicing by Overlap Extension," Gene, 77:61-68 (1989).

Jayaraman, et al, "Polymerase Chain Reaction-Mediated Gene Synthesis: Synthesis of a Gene Coding for Isozyme C of Horseradish Peroxidase," Porceedings of the National Academy of Sciences of the USA, 88(10):4084-4088 (1991).

Jayaraman, et al., "A PCR-Mediated Gene Synthesis Strategy Involving the Assembly of Oligonucleotides Representing Only One of the Strands," Biotechniques, 12(3):392-398 (1992).

Prodromou, et al., "Recursive PCR: A Novel Technique for Total Gene Synthesis," Gene Engineering, 5(8):827-829 (1992).

* cited by examiner

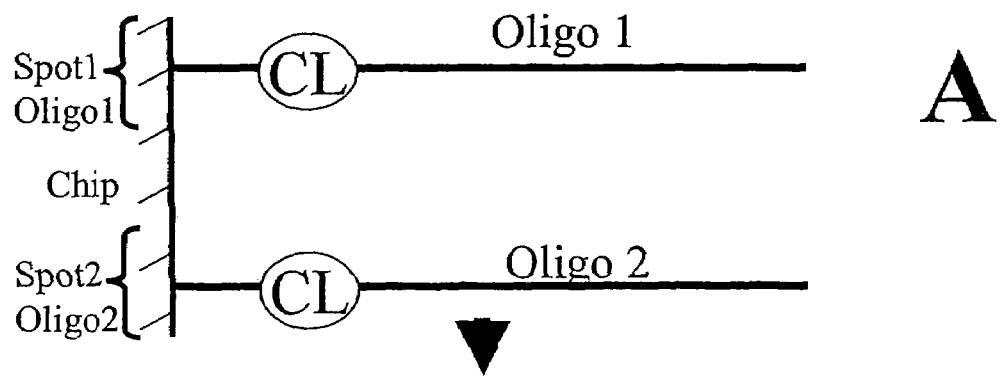
Chemical cleavage at cleavable linker CL recreate 5' or 3' end of specific oligos (1, 2, ...N). Oligos are released into a mixture and used for assembly.
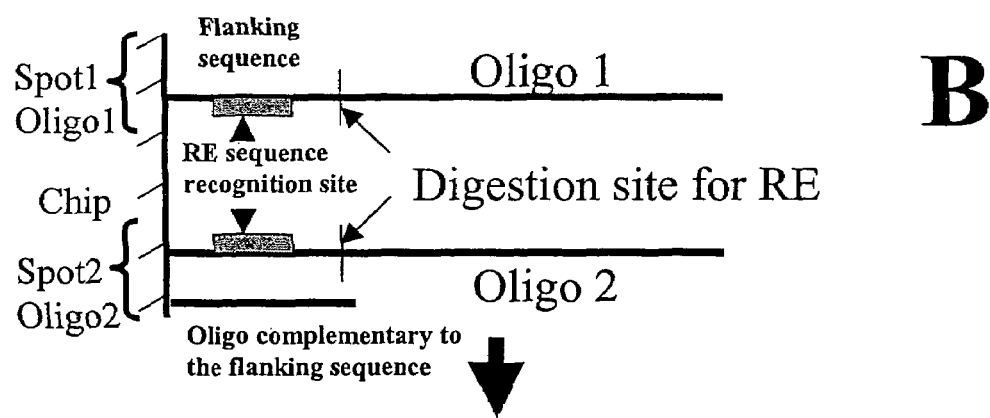
Hybridization to oligo complementary to the flanking sequence
Digestion with RE releases specific oligos into a mixture. This mixture is used for assembly
Figure 3

Cleavable linker for oligonucleotide synthesis

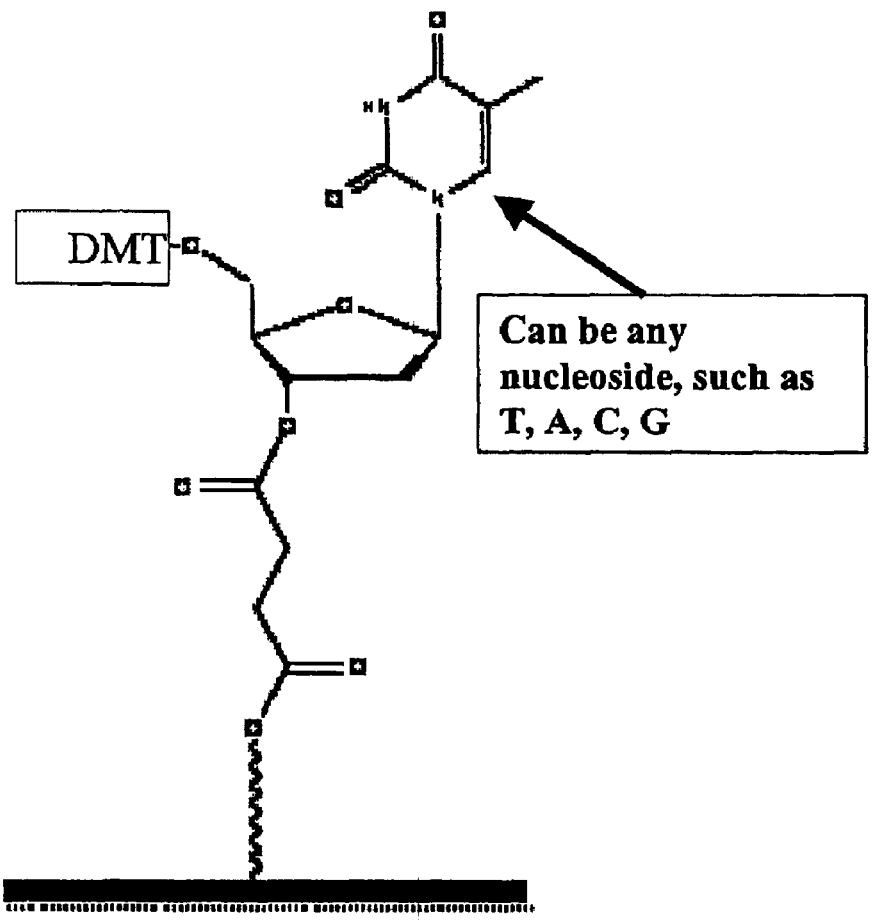

Shown is 5'-dimetoxytrityl-thymidine-3'succinate
Can be other nucleosides, such as A, G, C
T = 5'-dimetoxytrityl-thymidine-3'succinate
dC = 4-N-benzoyl-5'-dimethoxytrityl-deoxycytidine-3'-succinate,
dA = 1-N-benzoyl-5'-dimethoxytrityl-deoxyadenosine-3'-succinate,
dG = 2-N-isobutyryl-5'-dimethoxytrityl-deoxyguanosone-3'-succinate

Figure 3 A

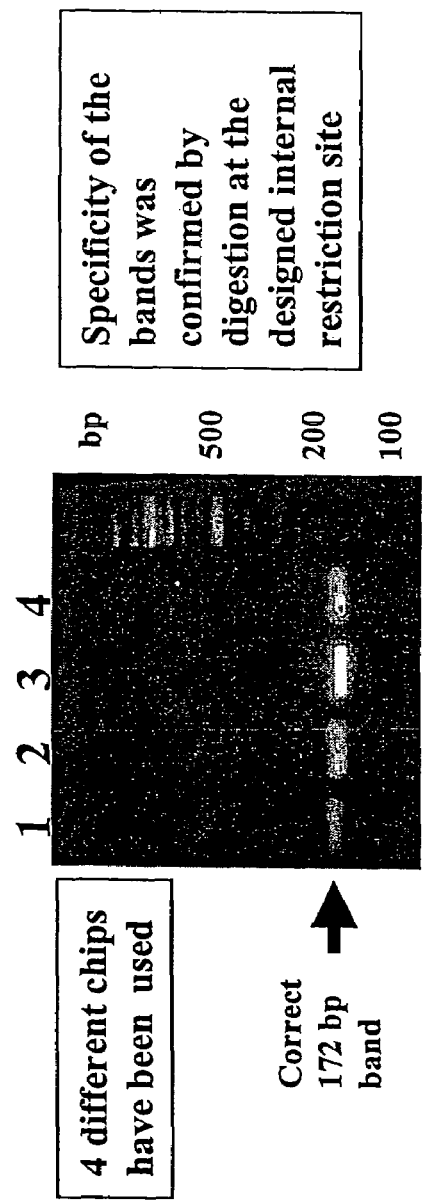
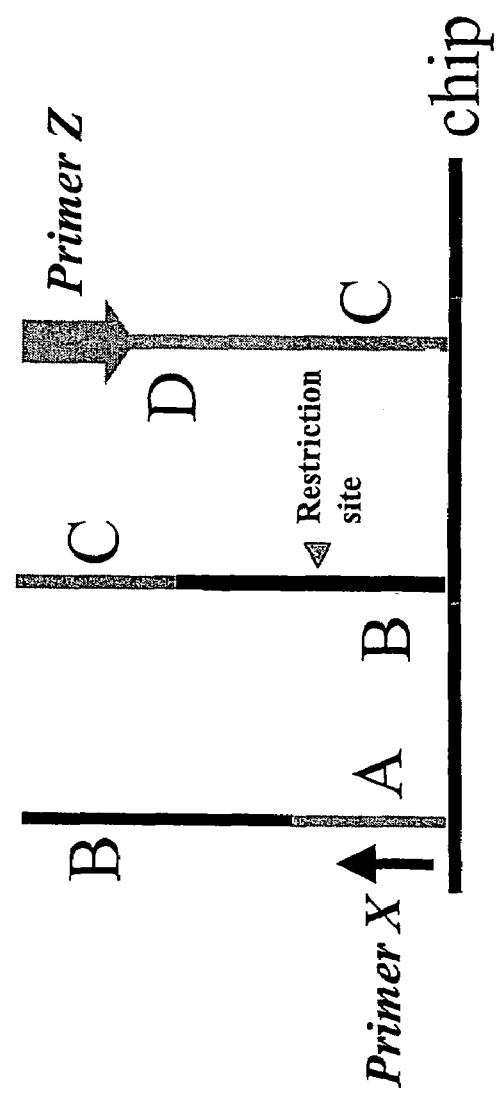
Figure 4

1
Chip-          Primer X
3'TAATTATGCTGAgTGATATCCCTTTCTACCTGTGCGGCTGGCGGACGACGA
AGTCGAATGTGGAGGGCCGTCTAAGGTGTCT5' (82mer)

2
Chip-                                        HpaII-site
3'GGACGACGAAGTCGAATGTGGAG*GGCC*GTCTAAGGTGTCTTAAAGTAT
CGACTGATGAAACTCTGCTCGTCGGTCACGAGGTTC-5' (84mer)

3
CHIP-
3'GTATCGACTGATGAAACTCTGCTCGTCGGTCACGAGGTTCCCTCGACCA
CCGCATGATGTTTCTGCTACTGCTGTTCACGATTATC-5' (86mer)
                           Primer Z Final product: 172mer (one of two strands is shown, direction is 3' to 5' for convenience)

3'TAATTATGCTGAgTGATATCCCTTTCTACCTGTGCGGCTGGCGGACGACGA
AGTCGAATGTGGAG*GGCC*GTCTAAGGTGTCTTAAAGTATCGACTGATGA
AACTCTGCTCGTCGGTCACGAGGTTCCCTCGACCACCGCATGATGTTTCTG
CTACTGCTGTTCACGATTATC5'

Figure 5

1: CCATCACGCTGAGTCTTACGTACGTAATACGACTCACTATAGGGAAAGTCGCCACCATGGACACGCCGACGAGACGACTCCTAATCGAA

2: CCATCACGCTGAGTCTTACGCCCTGTCTTCAGCTACACCTCCCGGCAGATTCCACAGAATTCGAGACGACTCCTAATCGAA

3: CCATCACGCTGAGTCTTACGATAGCTGACTACTTTGAGACGAGCAGCCAGTGCTCCAAGCCGGTGTCGAGACGACTCCTAATCGAA

4: CCATCACGCTGAGTCTTACGATCTTCCTAACCAAGCGAAGCCGGCAGGTCTGTGCTGACCCGAGACGACTCCTAATCGAA

5: CCATCACGCTGAGTCTTACGCAGGCACTCAGCTCTACGGGGCCGTCGCCGATGGGGTGTTCTGCTGTGGTAGTGGTCGGCAGCTGCATATTTCTGACCCACTCCTCACTGAGACGACTCCTAATCGAAC

6: CCATCACGCTGAGTCTTACGATATTTCTGGACCCTGCAGCACAGACCTCCCTCACTGGGTCAGCCGAGACGACTCCTAATCGAA

7: CCATCACGCTGAGTCTTACGGGCTTCGCTTGGTTAGGAAGATGACACCGGGCTTGGAGCACTGGCGAGACGACTCCTAATCGAA

8: CCATCACGCTGAGTCTTACGTGCTCGTCTCAAAGTAGTCAGCTATGAAATTCGTGAATCGCCGAGACGACTCCTAATCGAA

9: CCATCACGCTGAGTCTTACGGGGAGGTGTAGCTGAAGCAGCAGGCGGTCGGCCGTGTCCATGTGGCGACGAGACGACTCCTAATCGAA

Figure 8

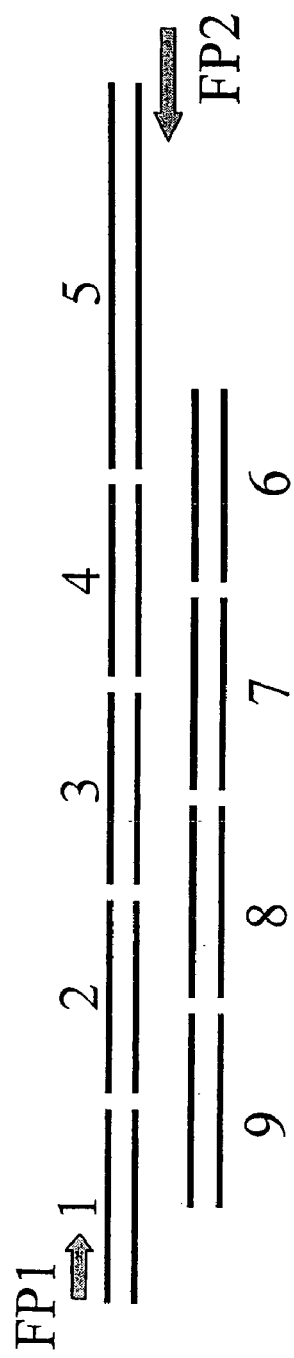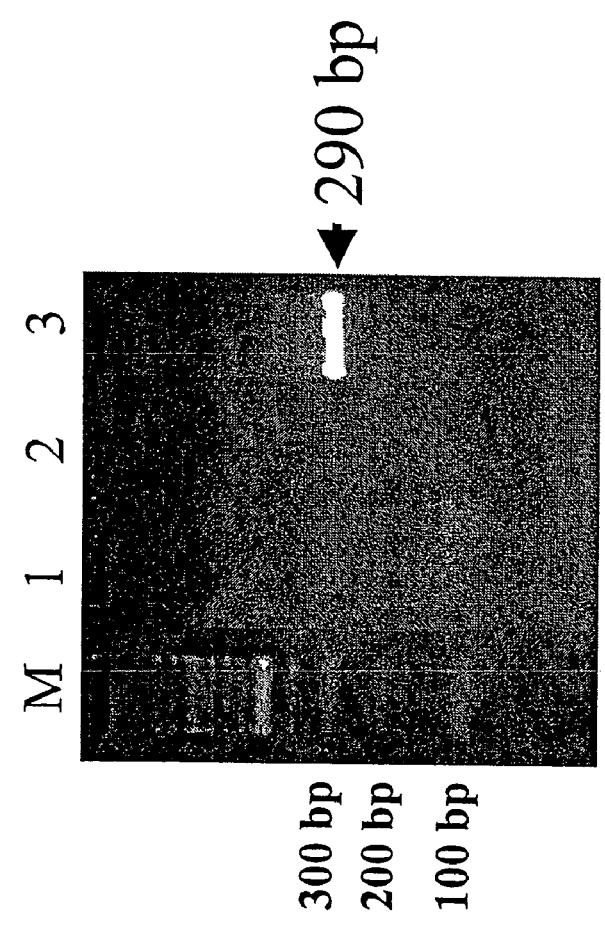
FP1 and FP2 are final primers 1 and 2 used to PCR the target sequence
Figure 9

1: TACGTAATACGACTCACTATAGGGAAAGTCGCCACCATGGACACGCCGAC

2: CGCCTGCTGCTTCAGCTACACCTCCCGGCAGATTCCACAGAATTTC

3: ATAGCTGACTACTTTGAGACGAGCAGCCAGTGCTCCAAGCCCGGTGTC

4: ATCTTCCTAACCAAGCGAAGCCGGCAGGTCTGTGCTGACCCC

5: AGTGAGGAGTGGGTCCAGAAATATGTCAGCGACCTAGAGCTGAGTGC

6: ATATTCTGGACCCACTCCTCACTGGGGTCAGCACAGACCTGCC

7: GGCTTCGCTTGGTTAGGAAGATGACACCGGGCTTGGAGCACTGGC

8: TGCTCGTCTCAAAGTAGTCAGCTATGAAATTCTGTGGAATCTGCC

9: GGGAGGTGTAGCTGAAGCAGCAGGCGGTCGGCGTGTCCATGGTGGCGAC

1F: GGTGAACAGCTCCTCGCCCTTGCTCACCATGGCACTCAGCTCTAGGTCGCTGAC

2F: CATGGTGAGCAAGGGCGAGGAGCTGTTCACCGGGGTGGTGCCCATCCTGGTC

3F: TTGTGGCCGTTTACGTCGCCGTCCAGCTCGACCAGGATGGGCACCACCCC

4F: GAGCTGGACGGCGACGTAAACGGCCACAAGTTCAGCGTGTCCGGCGAGGGC

5F: TTGCCGTAGGTGGCATCGCCCTCGCCCTCGCCGGACACGCTGAAC

6F: GAGGGCGATGCCACCTACGGCAAGCTGACCCTGAAGTTCATCTGCACC

7F: CAGGGCACGGGCAGCTTGCCGGTGGTGCAGATGAACTTCAGGGTCAGC

8F: ACCGGCAAGCTGCCCGTGCCCTGGCCCACCCTCGTGACCACCCTGACCTACGGC

9F: GGGGTAGCGGCTGAAGCACTGCACGCCGTAGGTCAGGGTGGTCACGAGGGTGGGC

10F: GTGCAGTGCTTCAGCCGCTACCCCGACCACATGAAGCAGCACGACTTC

11F: GTAGCCTTCGGGCATGGCGGACTTGAAGAAGTCGTGCTGCTTCATGTGGTC

12F: TTCAAGTCCGCCATGCCCGAAGGCTACGTCCAGGAGCGCACCATCTTCTTC

13F: GGGTCTTGTAGTTGCCGTCGTCCTTGAAGAAGATGGTGCGCTCCTGGAC

Figure 10 (continued)

14F: AAGGACGACGGCAACTACAAGACCCGCGCCGAGGTGAAGTTCGAGGGC

15F: AGCTCGATGCGGTTCACCAGGGTGTCGCCCTCGAACTTCACCTCGGCGC

16F: GACACCCTGGTGAACCGCATCGAGCTGAAGGGCATCGACTTCAAGGAGGAC

17F: TCCAGCTTGTGCCCCAGGATGTTGCCGTCCTCCTTGAAGTCGATGCCCTTC

18F: GGCAACATCCTGGGGCACAAGCTGGAGTACAACTACAACAGCCACAACGTC

19F: GTTCTTCTGCTTGTCGGCCATGATATAGACGTTGTGGCTGTTGTAGTTGTAC

20F: TATATCATGGCCGACAAGCAGAAGAACGGCATCAAGGTGAACTTCAAGATC

21F: ACGCTGCCGTCCTCGATGTTGTGGCGGATCTTGAAGTTCACCTTGATGCC

22F: CGCCACAACATCGAGGACGGCAGCGTGCAGCTCGCCGACCACTACCAGC

23F: ACGGGGCCGTCGCCGATGGGGGTGTTCTGCTGGTAGTGGTCGGCGAGCTGC

24F: AGAACACCCCATCGGCGACGGCCCCGTGCTGCTGCCCGACAACCACTACC

25F: TTTGCTCAGGGCGGACTGGGTGCTCAGGTAGTGGTTGTCGGGCAGCAGC

26F: TGAGCACCCAGTCCGCCCTGAGCAAAGACCCCAACGAGAAGCGCGATCAC

27F: GGCGGTCACGAACTCCAGCAGGACCATGTGATCGCGCTTCTCGTTGGGGTC

28F: ATGGTCCTGCTGGAGTTCGTGACCGCCGCCGGGATCACTCTCGGCATGGAC

29F: GGCGGCCGCTTTACTTGTACAGCTCGTCCATGCCGAGAGTGATCCCGGC

Figure 10
(continuation)

MICROARRAY SYNTHESIS AND ASSEMBLY OF GENE-LENGTH POLYNUCLEOTIDES

RELATED APPLICATIONS

This application is a continuation of U.S. application Ser. No. 10/243,367, filed Sep. 12, 2002, which is hereby incorporated by reference in its entirety.

TECHNICAL FIELD OF THE INVENTION

The present invention provides a process for in vitro synthesis and assembly of long, gene-length polynucleotides based upon assembly of multiple shorter oligonucleotides synthesized in situ on a microarray platform. Specifically, the present invention provides a process for in situ synthesis of oligonucleotide sequence fragments on a solid phase microarray platform and subsequent, "on chip" assembly of larger polynucleotides composed of a plurality of smaller oligonucleotide sequence fragments.

BACKGROUND OF THE INVENTION

In the world of microarrays, biological molecules (e.g., oligonucleotides, polypeptides and the like) are placed onto surfaces at defined locations for potential binding with target samples of nucleotides or receptors. Microarrays are miniaturized arrays of biomolecules available or being developed on a variety of platforms. Much of the initial focus for these microarrays have been in genomics with an emphasis of single nucleotide polymorphisms (SNPs) and genomic DNA detection/validation, functional genomics and proteomics (Wilgenbus and Lichter, *J. Mol. Med.* 77:761, 1999; Ashfari et al., *Cancer Res.* 59:4759, 1999; Kurian et al., *J. Pathol.* 187:267, 1999; Hacia, *Nature Genetics* 21 suppl.:42, 1999; Hacia et al., *Mol. Psychiatry* 3:483, 1998; and Johnson, *Curr. Biol.* 26:R171, 1998).

There are, in general, three categories of microarrays (also called "biochips" and "DNA Arrays" and "Gene Chips" but this descriptive name has been attempted to be a trademark) having oligonucleotide content. Most often, the oligonucleotide microarrays have a solid surface, usually silicon-based and most often a glass microscopic slide. Oligonucleotide microarrays are often made by different techniques, including (1) "spotting" by depositing single nucleotides for in situ synthesis or completed oligonucleotides by physical means (ink jet printing and the like), (2) photolithographic techniques for in situ oligonucleotide synthesis (see, for example, Fodor U.S. Pat. No. '934 and the additional patents that claim priority from this priority document, (3) electrochemical in situ synthesis based upon pH based removal of blocking chemical functional groups (see, for example, Montgomery U.S. Pat. No. 6,092,302 the disclosure of which is incorporated by reference herein and Southern U.S. Pat. No. 5,667,667), and (4) electric field attraction/repulsion of fully-formed oligonucleotides (see, for example, Hollis et al., U.S. Pat. No. 5,653,939 and its duplicate Heller U.S. Pat. No. 5,929,208). Only the first three basic techniques can form oligonucleotides in situ e.g., building each oligonucleotide, nucleotide-by-nucleotide, on the microarray surface without placing or attracting fully formed oligonucleotides.

With regard to placing fully formed oligonucleotides at specific locations, various micro-spotting techniques using computer-controlled plotters or even ink-jet printers have been developed to spot oligonucleotides at defined locations. One technique loads glass fibers having multiple capillaries drilled through them with different oligonucleotides loaded into each capillary tube. Microarray chips, often simply glass microscope slides, are then stamped out much like a rubber stamp on each sheet of paper of glass slide. It is also possible to use "spotting" techniques to build oligonucleotides in situ. Essentially, this involves "spotting" relevant single nucleotides at the exact location or region on a slide (preferably a glass slide) where a particular sequence of oligonucleotide is to be built. Therefore, irrespective of whether or not fully formed oligonucleotides or single nucleotides are added for in situ synthesis, spotting techniques involve the precise placement of materials at specific sites or regions using automated techniques.

Another technique involves a photolithography process involving photomasks to build oligonucleotides in situ, base-by-base, by providing a series of precise photomasks coordinated with single nucleotide bases having light-cleavable blocking groups. This technique is described in Fodor et al., U.S. Pat. No. 5,445,934 and its various progeny patents. Essentially, this technique provides for "solid-phase chemistry, photolabile protecting groups, and photolithography . . . to achieve light-directed spatially-addressable parallel chemical synthesis."

The electrochemistry platform (Montgomery U.S. Pat. No. 6,092,302, the disclosure of which is incorporated by reference herein) provides a microarray based upon a semiconductor chip platform having a plurality of microelectrodes. This chip design uses Complimentary Metal Oxide Semiconductor (CMOS) technology to create high-density arrays of microelectrodes with parallel addressing for selecting and controlling individual microelectrodes within the array. The electrodes turned on with current flow generate electrochemical reagents (particularly acidic protons) to alter the pH in a small "virtual flask" region or volume adjacent to the electrode. The microarray is coated with a porous matrix for a reaction layer material. Thickness and porosity of the material is carefully controlled and biomolecules are synthesized within volumes of the porous matrix whose pH has been altered through controlled diffusion of protons generated electrochemically and whose diffusion is limited by diffusion coefficients and the buffering capacities of solutions. However, in order to function properly, the microarray biochips using electrochemistry means for in situ synthesis has to alternate anodes and cathodes in the array in order to generated needed protons (acids) at the anodes so that the protons and other acidic electrochemically generated acidic reagents will cause an acid pH shift and remove a blocking group from a growing oligomer.

Gene Assembly

The preparation of arbitrary polynucleotide sequences is useful in a "post-genomic" era because it provides any desirable gene oligonucleotide or its fragment, or even whole genome material of plasmids, phages and viruses. Such polynucleotides are long, such as in excess of 1000 bases in length. In vitro synthesis of oligonucleotides (given even the best yield conditions of phosphoramidite chemistry) would not be feasible because each base addition reaction is less than 100% yield. Therefore, researchers desiring to obtain long polynucleotides of gene length or longer had to turn to nature or gene isolation techniques to obtain polynucleotides of such length. For the purposes of this patent application, the term "polynucleotide" shall be used to refer to nucleic acids (either single stranded or double stranded) that are sufficiently long so as to be practically not feasible to make in vitro through single base addition. In view of the exponential drop-off in yields from nucleic acid synthesis chemistries, such as phosphoramidite chemistry, such polynucleotides generally have greater than 100 bases and often greater than 200 bases in length. It should be noted that many commercially useful gene cDNA's often have lengths in excess of 1000 bases.

Moreover, the term "oligonucleotides" or shorter term "oligos" shall be used to refer to shorter length single stranded or double stranded nucleic acids capable of in vitro synthesis and generally shorter than 150 bases in length. While it is theoretically possible to synthesize polynucleotides through single base addition, the yield losses make it a practical impossibility beyond 150 bases and certainly longer than 250 bases.

However, knowledge of the precise structure of the genetic material is often not sufficient to obtain this material from natural sources. Mature cDNA, which is a copy of an mRNA molecule, can be obtained if the starting material contains the desired mRNA. However, it is not always known if the particular mRNA is present in a sample or the amount of the mRNA might be too low to obtain the corresponding cDNA without significant difficulties. Also, different levels of homology or splice variants may interfere with obtaining one particular species of mRNA. On the other hand many genomic materials might be not appropriate to prepare mature gene (cDNA) due to exon-intron structure of genes in many different genomes.

In addition, there is a need in the art for polynucleotides not existing in nature to improve genomic research performance. In general, the ability to obtain a polynucleotide of any desired sequence just knowing the primary structure, for a reasonable price, in a short period of time, will significantly move forward several fields of biomedical research and clinical practice.

Assembly of long arbitrary polynucleotides from oligonucleotides synthesized by organic synthesis and individually purified has other problems. The assembly can be performed using PCR or ligation methods. The synthesis and purification of many different oligonucleotides by conventional methods (even using multi-channel synthesizers) are laborious and expensive procedures. The current price of assembled polynucleotide on the market is about $12-25 per base pair, which can be considerable for assembling larger polynucleotides. Very often the amount of conventionally synthesized oligonucleotides would be excessive. This also contributes to the cost of the final product.

Therefore, there is a need in the art to provide cost-effective polynucleotides by procedures that are not as cumbersome and labor-intensive as present methods to be able to provide polynucleotides at costs below $1 per base or 1-20 times less than current methods. The present invention was made to address this need.

SUMMARY OF THE INVENTION

The present invention provides a process for the assembly of oligonucleotides synthesized on microarrays into a polynucleotide sequence. The desired target polynucleotide sequence is dissected into pieces of overlapping oligonucleotides. In the first embodiment these oligonucleotides are synthesized in situ, in parallel on a microarray chip in a non-cleavable form. A primer extension process assembles the target polynucleotides. The primer extension process uses starting primers that are specific for the appropriate sequences. The last step is PCR amplification of the final polynucleotide product. Preferably, the polynucleotide product is a cDNA suitable for transcription purposes and further comprising a promoter sequence for transcription.

The present invention provides a process for assembling a polynucleotide from a plurality of oligonucleotides comprising:

(a) synthesizing or spotting a plurality of oligonucleotide sequences on a microarray device or bead device having a solid or porous surface, wherein a first oligonucleotide is oligo 1 and a second oligonucleotide is oligo 2 and so on, wherein the plurality of oligonucleotide sequences are attached to the solid or porous surface, and wherein the first oligonucleotide sequence has an overlapping sequence region of from about 10 to about 50 bases that is the same or substantially the same as a region of a second oligonucleotide sequence, and wherein the second oligonucleotide sequence has an overlapping region with a third oligonucleotide sequence and so on;

(b) forming complementary oligo 1 by extending primer 1, wherein primer 1 is complementary to oligo 1;

(c) disassociating complementary oligo 1 from oligo 1 and annealing complementary oligo 1 to both oligo 1 and to the overlapping region of oligo 2, wherein the annealing of complementary oligo 1 to oligo 2 serves as a primer for extension for forming complementary oligo 1+2;

(d) repeating the primer extension cycles of step (c) until a full-length polynucleotide is produced; and (e) amplifying the assembled complementary full length polynucleotide to produce a full length polynucleotide in desired quantities.

Preferably, the solid or porous surface is in the form of a microarray device. Most preferably, the microarray device is a semiconductor device having a plurality of electrodes for synthesizing oligonucleotides in situ using electrochemical means to couple and decouple nucleotide bases. Preferably, the primer extension reaction is conducted through a sequential process of melting, annealing and then extension. Most preferably, the primer extension reaction is conducted in a PCR amplification device using the microarray having the plurality of oligonucleotides bound thereto.

The present invention further provides a process for assembling a polynucleotide from a plurality of oligonucleotides comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has an overlapping region corresponding to a next oligonucleotide sequence within the sequence and further comprises two flanking sequences, one at the 3' end and the other at the 5' end of each oligonucleotide, wherein each flanking sequence is from about 7 to about 50 bases and comprising a primer region and a sequence segment having a restriction enzyme cleavable site;

(b) amplifying each oligonucleotide using the primer regions of the flanking sequence to form double stranded (ds) oligonucleotides;

(c) cleaving the oligonucleotide sequences at the restriction enzyme cleavable site; and (d) assembling the cleaved oligonucleotide sequences through the overlapping regions to form a full length polynucleotide.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof. Preferably, the flanking sequence further comprises a binding moiety used to purify cleaved oligonucleotides from flanking sequences. Preferably, the process further comprises the step of labeling the flanking sequence during the amplification step (b) using primer sequences labeled with binding moieties. Most preferably, a binding moiety is a small molecule able to be captured, such as biotin captured by avidin or streptavidin, or fluorescein able to be captured by an anti-fluorescein antibody.

The present invention further provides a process for assembling a polynucleotide from a plurality of oligonucleotides comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has an overlapping region corresponding to a next oligonucleotide sequence within the sequence, and further comprises a sequence segment having a cleavable linker moiety;

(b) cleaving the oligonucleotide sequences at the cleavable linker site to cleave each oligonucleotide complex from the microarray or bead solid surface to form a soluble mixture of oligonucleotides, each having an overlapping sequence; and (c) assembling the oligonucleotide sequences through the overlapping regions to form a full length polynucleotide.

Preferably, the cleavable linker is a chemical composition having a succinate moiety bound to a nucleotide moiety such that cleavage produces a 3'hydroxy nucleotide. Most preferably, the cleavable linker is selected from the group consisting of 5'-dimethoxytrityl-thymidine-3'succinate, 4-N-benzoyl-5'-dimethoxytrityl-deoxycytidine-3'-succinate, 1-N-benzoyl-5'-dimethoxytrityl-deoxyadenosine-3'-succinate, 2-N-isobutyryl-5'-dimethoxytrityl-deoxyguanosone-3'-succinate, and combinations thereof.

The present invention further provides a process for assembling a polynucleotide from a plurality of oligonucleotides comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has a flanking region at an end attached to the solid or porous surface, and a specific region designed by dissecting the polynucleotide sequence into a plurality of overlapping oligonucleotides, wherein a first overlapping sequence on a first oligonucleotide corresponds to a second overlapping sequence of a second oligonucleotide, and wherein the flanking sequence comprises a sequence segment having a restriction endonuclease (RE) recognition sequence capable of being cleaved by a corresponding RE enzyme;

(b) hybridizing an oligonucleotide sequence complementary to the flanking region to form a double stranded sequence capable of interacting with the corresponding RE enzyme;

(c) digesting the plurality of oligonucleotides to cleave them from the microarray device or beads into a solution; and (d) assembling the oligonucleotide mixture through the overlapping regions to form a full length polynucleotide.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof. Preferably, the process further comprises a final step of amplifying the polynucleotide sequence using primers located at both ends of the polynucleotide.

The present invention further provides a process for creating a mixture of oligonucleotide sequences in solution comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence further comprises two flanking sequences, one at the 3' end and the other at the 5' end of each oligonucleotide, wherein each flanking sequence is from about 7 to about 50 bases and comprising a primer region and a sequence segment having a restriction enzyme cleavable site;

(b) amplifying each oligonucleotide using the primer regions of the flanking sequence to form a double stranded (ds) oligonucleotides; and (c) cleaving the double stranded oligonucleotide sequences at the restriction enzyme cleavable site.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof. Preferably, the flanking sequence further comprises a binding moiety used to purify cleaved oligonucleotides from flanking sequences. Preferably, the process further comprises the step of labeling the flanking sequence during the amplification step (b) using primer sequences labeled with binding moieties. Most preferably, a binding moiety is a small molecule able to be captured, such as biotin captured by avidin or streptavidin, or fluorescein able to be captured by an anti-fluorescein antibody.

The present invention further provides a process for creating a mixture of oligonucleotide sequences in solution comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has a sequence segment having a cleavable linker moiety;

(b) cleaving the oligonucleotide sequences at the cleavable linker site to cleave each oligonucleotide sequence from the microarray or bead solid surface to form a soluble mixture of oligonucleotides.

Preferably, the cleavable linker is a chemical composition having a succinate moiety bound to a nucleotide moiety such that cleavage produces a 3'hydroxy nucleotide. Most preferably, the cleavable linker is selected from the group consisting of 5'-dimethoxytrityl-thymidine-3'-succinate, 4-N-benzoyl-5'-dimethoxytrityl-deoxycytidine-3'-succinate, 1-N-benzoyl-5'-dimethoxytrityl-deoxyadenosine-3'-succinate, 2-N-isobutyryl-5'-dimethoxytrityl-deoxyguanosone-3'-succinate, and combinations thereof.

The present invention further provides a process for creating a mixture of oligonucleotide sequences in solution comprising:

(a) synthesizing in situ or spotting a plurality of oligonucleotide sequences on a microarray device or bead device each having a solid or porous surface, wherein the plurality of oligonucleotide sequences are attached to the solid or porous surface, and wherein each oligonucleotide sequence has a flanking region at an end attached to the solid or porous surface, and a specific region, wherein the flanking sequence comprises a sequence segment having a restriction endonuclease (RE) recognition sequence capable of being cleaved by a corresponding RE enzyme;

(b) hybridizing an oligonucleotide sequence complementary to the flanking region to form a double stranded sequence capable of interacting with the corresponding RE enzyme;

(c) digesting the plurality of oligonucleotides to cleave them from the microarray device or beads into a solution.

Preferably, the flanking sequence is from about 10 to about 20 bases in length. Preferably, the restriction enzyme cleavable site is a class II endonuclease restriction site sequence capable of being cleaved by its corresponding class II restriction endonuclease enzyme. Most preferably, the restriction endonuclease class II site corresponds to restriction sites for a restriction endonuclease class II enzyme selected from the group consisting of Mly I, BspM I, Bae I, BsaX I, Bsr I, Bmr I, Btr I, Bts I, Fok I, and combinations thereof.

BRIEF DESCRIPTION OF THE DRAWINGS

FIG. 1 shows a schematic of gene assembly on a microarray device surface or porous matrix. FIG. 1A also shows, relative to the target sequence, primer Pr1; extension product of primer Pr1, which is complementary to oligonucleotide 1; and extension product of complementary oligonucleotide 1, which is complementary to oligonucleotides 1+2.

FIG. 3 shows a schematic for gene assembly using oligos synthesized and then cleaved from a microarray device. Specifically, in the upper panel marked "A", oligonucleotide sequences are connected to the microarray device through a cleavable linker (CL) moiety. An example of a cleavable linker moiety is provided in FIG. 3A. The cleavable linkers are molecules that can withstand the oligonucleotide synthesis process (i.e., phosphoramidite chemistry) and then can be cleaved to release oligonucleotide fragments. Chemical cleavage at cleavable linker CL recreates usual 3' end of specific oligos 1 through N. These oligonucleotides are released into a mixture. The mixture of oligonucleotides is subsequently assembled into full-length polynucleotide molecules. In the lower panel marked "B" of FIG. 3, oligonucleotide sequences are connected to the microarray device through additional flanking sequence containing a restriction enzyme (RE) sequence site. Another oligonucleotide sequence, complementary to the flanking sequence region, is hybridized to the oligonucleotides on the microarray device. This recreates a "ds" or double-stranded oligonucleotide structure, each having a RE sequence recognition region in the flanking sequence region. Digestion of this ds oligonucleotides with the corresponding RE enzymes at the RE recognition sites in the flanking sequence regions releases the specific oligonucleotides 1 through N. When assembled, oligonucleotide sequences 1 through N form a full-length polynucleotide molecule.

FIG. 4 shows the assembly of a polynucleotide from three oligonucleotide fragments wherein each oligonucleotide fragment was synthesized in situ on a microarray device. The fully assembled polynucleotide was 172 mers in length, a length not practically achievable by in situ synthesis. The first embodiment inventive process was used in this example.

FIG. 5 shows the oligonucleotide sequences used to assemble the 172-mer polynucleotide of FIG. 4 (oligonucleotide #1 (SEQ ID NO: 1), oligonucleotide #2 (SEQ ID NO: 2), oligonucleotide #3 (SEQ ID NO: 3). final product (SEQ ID NO: 4)). The sequences of primers X and Z are underlined. The Hpa II restriction site is indicated by italic underlined letters.

FIG. 8 shows the sequences from nine oligonucleotides fragments (consecutively numbered 1-9 (SEQ ID NOs: 5-13)) used to assemble a 290 bp polynucleotide. The flanking regions are shown in bold and underlined. The process used for polynucleotide assembly was the second embodiment. The overlapping regions further contained a cleavable site as the MlyI recognition site for the MlyI class II restriction endonuclease.

FIG. 9 shows a schematic in the top panel for assembling a polynucleotide from nine oligonucleotides. Nine oligonucleotide sequences, shown in FIG. 8, were amplified by PCR using primers 1 and 2 (as described in FIG. 6) into ds DNA fragments containing the same flanking regions and specific overlapping sequences, digested with MlyI enzyme to remove flanking sequences, and used for assembly of 290 bp DNA fragment. The columns in the gel shown are M—markers, 1—negative control, assembly without primers FP1 and FP2, 2—negative control, assembly without specific oligos, 3—assembly of 290 bp fragment from specific oligos plus amplification with FP1 and FP2 primers. The band in column 3 shows a high efficiency of the inventive polynucleotide assembly process.

FIG. 10 shows a sequence of an assembled polynucleotide in Example 4, broken down into its component oligonucleotides (fragments 1-9 (SEQ ID NOs: 14-22) and fragments 1F-29F (SEQ ID NOs: 23-51).

DETAILED DESCRIPTION OF THE INVENTION

Figure 1A:
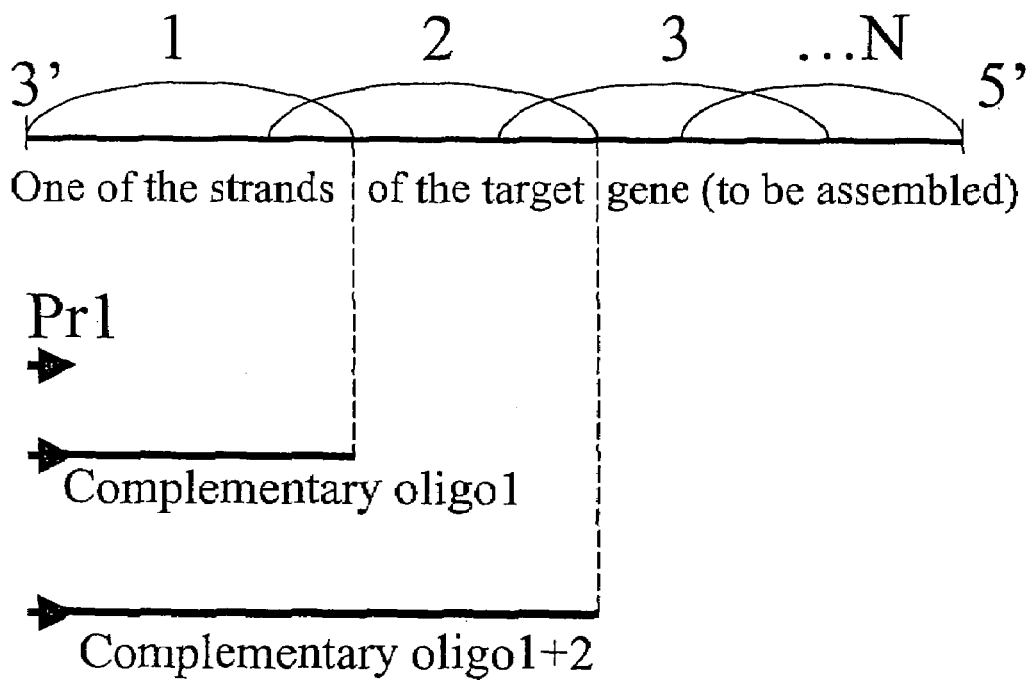
In FIG. 1A, the target gene sequence is dissected into number of overlapping oligonucleotides. The 3' and 5' are the ends of the shown strand.

The present invention describes the preparation of a polynucleotide sequence (also called "gene") using assembly of overlapping shorter oligonucleotides synthesized or spotted on microarray devices or on solid surface bead devices. The shorter oligonucleotides include sequence regions having overlapping regions to assist in assembly into the sequence of the desired polynucleotide. Overlapping regions refer to sequence regions at either a 3' end or a 5' end of a first oligonucleotide sequence that is the same as part of the second oligonucleotide and has the same direction (relative to 3' to 5' or 5' to 3' direction), and will hybridize to the 5' end or 3' end of a second oligonucleotide sequence or its complementary sequence (second embodiment), and a second oligonucleotide sequence to a third oligonucleotide sequence, and so on. In order to design or develop a microarray device or bead device to be used for polynucleotide assembly, the polynucleotide sequence is divided (or dissected) into a number of overlapping oligonucleotides segments, each with lengths preferably from 20 to 1000 bases, and most preferably from 20 to 200 bases (FIG. 1A). The overlap between oligonucleotide segments is 5 or more bases, preferably 15-25 bases to that proper hybridization of first to second, second to third, third to fourth and so on occurs. These oligonucleotides (or oligos) are preferably synthesized on a microarray device using any available method (i.e., electrochemical in situ synthesis, photolithography in situ synthesis, ink-jet printing, spotting, etc.). The direction of synthesis relative to the microarray device surface or porous matrix covering a microarray device can be from 3' to 5' or from 5' to 3'. Preferably, in situ synthesis is done in the 3' to 5' direction.

In the first embodiment the inventive gene/polynucleotide assembly process uses oligonucleotides immobilized on a microarray device. The microarray device itself or a porous reaction layer with immobilized oligonucleotides can be used for the inventive gene/polynucleotide assembly process.

Figure 1B:
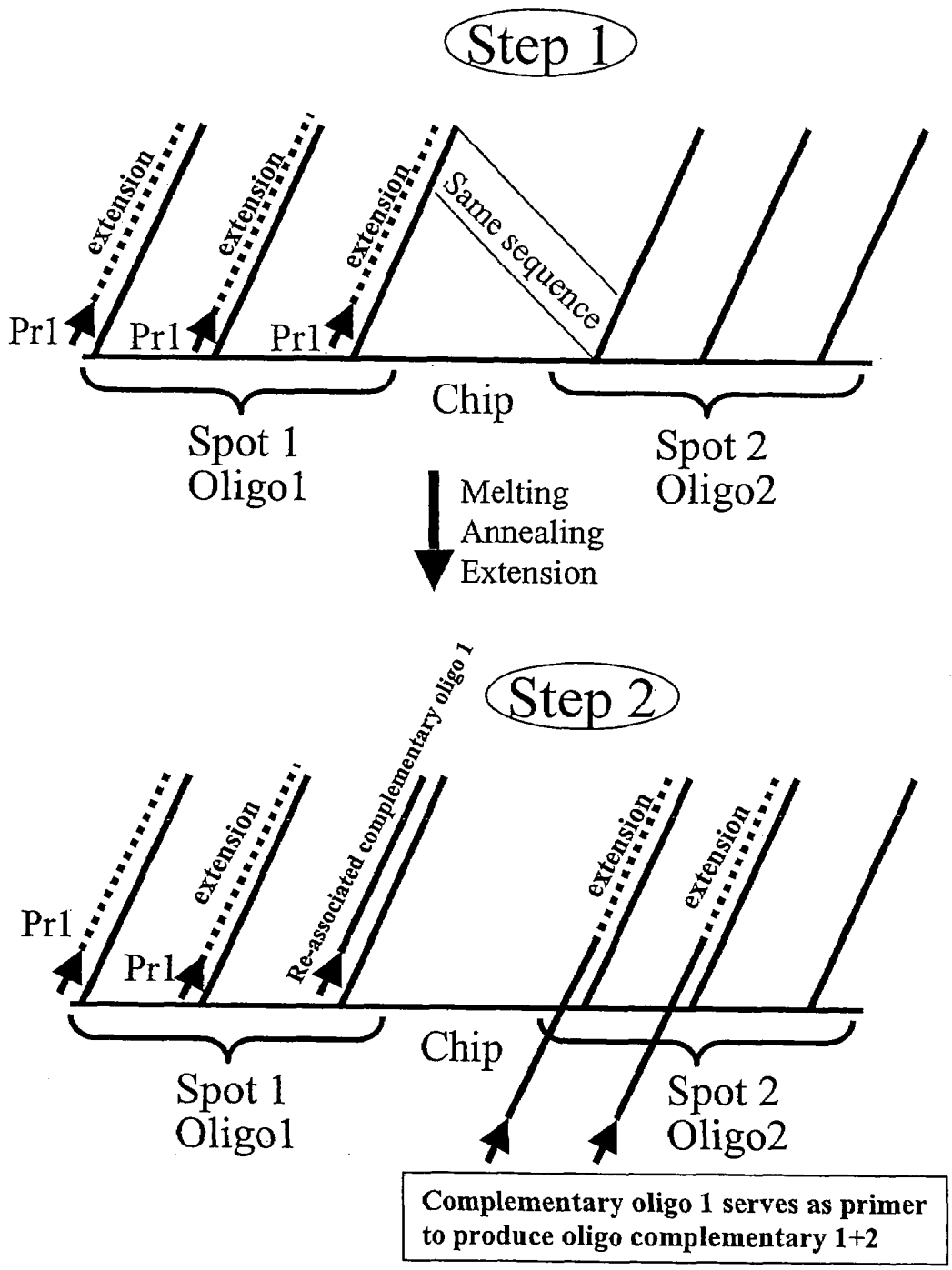
FIG. 1B illustrates one embodiment of the initial steps of an assembly process. In step 1 of assembly, Primer Pr1 is annealed to oligonucleotide 1 and extended by appropriate polymerase enzyme into product complementary to oligonucleotide 1. The second step is melting, re-annealing and extension (i.e., amplification) to lead to production of larger amount of Pr1 extension product (complementary oligonucleotide 1), re-association of the complementary oligonucleotide 1 with oligonucleotide 1, and to annealing of the complementary oligonucleotide 1 with oligonucleotide 2 followed by its extension into product complementary to oligonucleotides 1+2.

With regard to FIG. 1B, the process comprises several repeated steps of melting, annealing and extension (FIG. 1B), which can be performed in any thermal cycle instrument. The cycling program is similar to the programs used for PCR. At the first step of gene/polynucleotide assembly, primer Pr1 is added and anneals to oligonucleotide 1 on the microarray device and then extends by appropriate polymerase enzyme into product complementary to oligonucleotide 1 (called complementary oligonucleotide 1). At the second step of the process the product complementary to oligonucleotide 1 is melted from oligonucleotide 1, primer Pr1 is annealed again to the oligonucleotide 1 as well as product complementary to oligonucleotide 1 is partially re-anneals to oligonucleotide 1 and partially anneals to oligonucleotide 2 due to an overlapping sequence region between oligonucleotide 1 and oligonucleotide 2. Extension of Pr1 leads to production of an additional amount of Pr1 extension product (complementary oligonucleotide 1). The annealing of the complementary oligonucleotide 1 to oligonucleotide 2 followed by its extension leads to product complementary to oligonucleotides 1+2 (called complementary oligonucleotides 1+2). Similarly, at step 3 of the process melting, re-annealing and extension lead to the same products as at step 2 plus a product complementary to oligonucleotides 1+2+3. These cycles of melting, annealing and extension are repeated until full-length polynucleotide is formed. The number of cycles should be equal or more than the number of oligos on microarray device. After formation, the final target polynucleotide molecule is amplified by a PCR process with two primers complementary to the ends of this molecule to the desirable amounts.

In a second embodiment, a plurality of oligonucleotides that together comprise (with overlapping regions) the target polynucleotide sequence are synthesized on a microarray device (or can be synthesized on beads as a solid substrate), wherein each oligonucleotide sequence further comprises flanking short sequence regions, wherein each flanking sequence region comprises one or a plurality of sequence sites for restriction endonuclease, preferably endonuclease class II (ERII) enzymes. Each oligonucleotide is amplified by PCR using appropriate oligonucleotide primers to the flanking sequence regions to form a preparation of a plurality of oligonucleotides. The preparation of oligonucleotides is treated then with appropriate REII enzyme(s) (specific to the restriction sequences in the flanking sequence regions) to produce flanking fragments and overlapping oligonucleotides that, together comprise the desired polynucleotide sequence. Flanking fragments and PCR primers are removed from the mixture, if desired, by different methods based on size or specific labeling of the PCR primers. The oligonucleotides resembling the desired target polynucleotide then assembled into the final target polynucleotide molecule using repetition of the primer extension method and PCR amplification of the final molecule.

Figure 2:
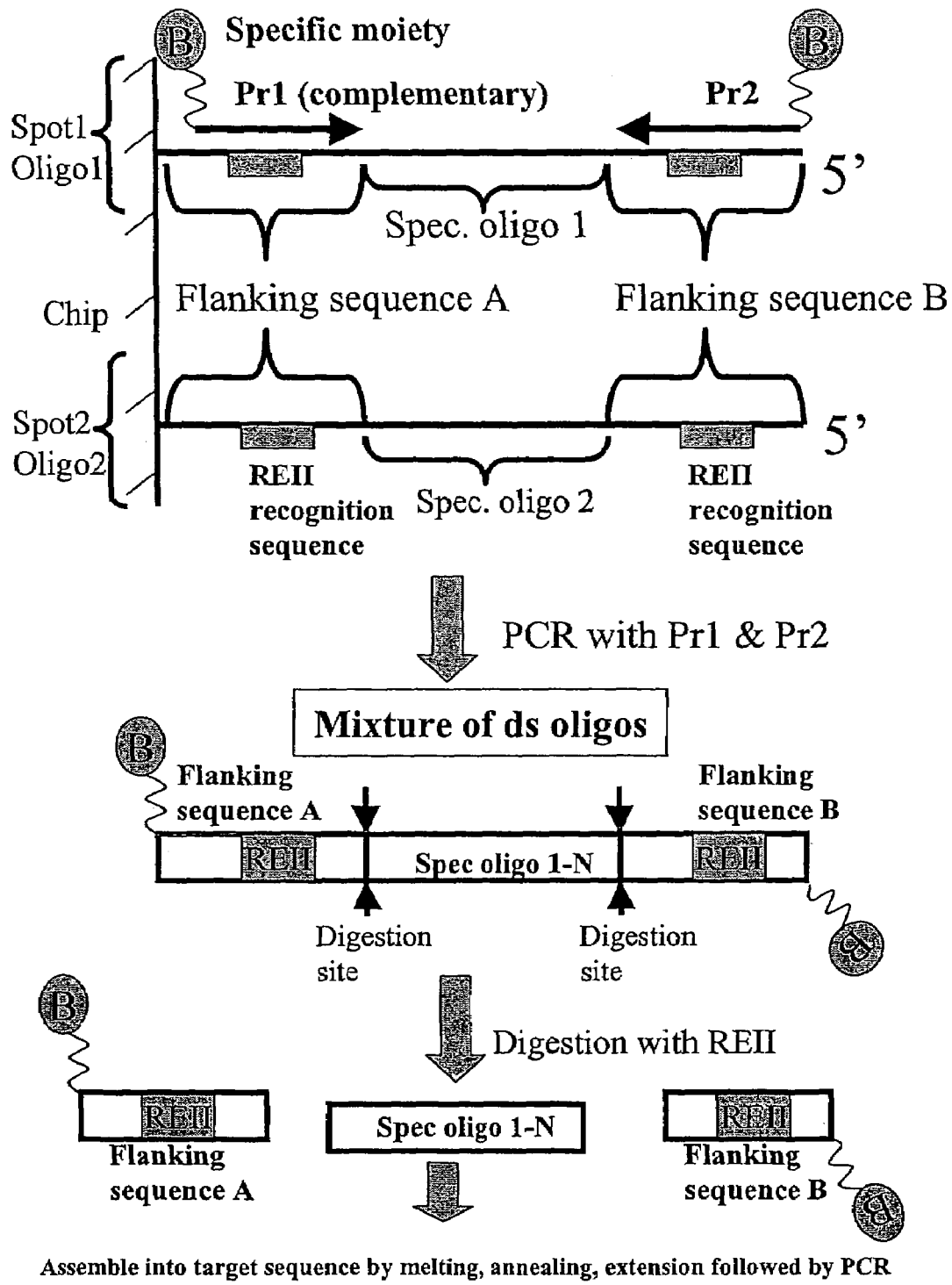
FIG. 2 shows a second embodiment of the inventive gene assembly process using oligonucleotides synthesized in situ onto a microarray device, each having a flanking sequence region containing a restriction enzyme cleavage site, followed by a PCR amplification step and followed by a REII restriction enzyme cleavage step.

Specifically, in the second embodiment, the assembly process initially uses oligonucleotides immobilized on a microarray device or beads, via immobilization techniques, such as spotting or ink-jet printing or by direct in situ synthesis of the microarray device using various techniques, such as photolithography or electrochemical synthesis. The overlapping oligonucleotide sequences are designed having an overlapping region and one or two flanking sequence regions comprising a restriction class II recognition site (FIG. 2A). The assembled oligonucleotides together comprise the target polynucleotide sequence.

The length of flanking sequences is at least the length of REII recognition site. The flanking sequences are designed to have minimal homology to the specific oligonucleotide sequences regions on the microarray device. The flanking sequences can be the same for each oligonucleotide fragment, or be two or more different sequences. For example, a pair of appropriate primers, called Pr1 and Pr2, was designed to amplify each oligonucleotide on a microarray device (FIG. 2) by PCR. Each primer may contain a binding moiety, such as biotin, that does not affect their ability to serve as primers. After PCR amplification the amplified ds copy of each oligonucleotide was present in the reaction mixture. This reaction mixture was treated with the appropriate REII enzyme or enzymes specific for the restriction sites in the flanking sequence regions. The digestion sites for REII were designed, after cleavage, to produce the desired specific oligonucleotide sequence fragments that, when assembled will form the target polynucleotide sequence. As a result of digestion a mixture of specific double stranded (ds) overlapping oligonucleotide sequence fragments resembling the structure of desired target polynucleotide, and ds flanking sequences were formed. If desired, these flanking sequences and residual primers are, removed from the mixture using specific absorption through specific moieties introduced in the primers (such as, for example, by absorption on avidin beads for biotin-labeled primers), or based on the size difference of the specific oligos and flanking sequences and primers. The mixture of specific oligonucleotide sequences resembling target gene sequence is used to assemble the final target polynucleotide molecule using repeated cycles of melting, self-annealing and polymerase extension followed by PCR amplification of the final target polynucleotide molecule with appropriate PCR primers designed to amplify. This final PCR amplification step is routinely done in the art and described in, for example, Mullis et al., *Cold Spring Harb. Symp. Quant. Biol.* 51 Pt 1:263-73, 1986; and Saiki et al., *Science* 239:487-91, 1988. PCR amplification steps generally follow manufacturer's instructions. Briefly, A process for amplifying any target nucleic acid sequence contained in a nucleic acid or mixture thereof comprises treating separate complementary strands of the nucleic acid with a molar excess of two oligonucleotide primers and extending the primers with a thermostable enzyme to form complementary primer extension products which act as templates for synthesizing the desired nucleic acid sequence. The amplified sequence can be readily detected. The steps of the reaction can be repeated as often as desired and involve temperature cycling to effect hybridization, promotion of activity of the enzyme, and denaturation of the hybrids formed.

In another embodiment for the assembly step, oligonucleotide sequences that together comprise the target polynucleotide molecule are assembled using a ligase chain reaction as described in Au et al., *Biochem. Biophys. Res. Commun.* 248:200-3, 1998. Briefly, short oligonucleotides are joined through ligase chain reaction (LCR) in high stringency conditions to make "unit fragments" (Fifty microliters of reaction mixture contained 2.2 mM of each oligo, 8 units Pfu DNA ligase (Stratagene La Jolla, Calif.) and reaction buffer provided with the enzyme. LCR was conducted as follows: 95° C. 1 min; 55° C. 1.5 min, 70° C. 1.5 min, 95° C. 30 sec for 15 cycles; 55° C. 2 min, which are then fused to form a full-length gene sequence by polymerase chain reaction.

In another embodiment the ds oligonucleotide sequences are assembled after preparation by chain ligation cloning as described in Pachuk et al., *Gene* 243:19-25, 2000; and U.S. Pat. No. 6,143,527 (the disclosure of which is incorporated by reference herein). Briefly, chain reaction cloning allows ligation of double-stranded DNA molecules by DNA ligases and bridging oligonucleotides. Double-stranded nucleic acid molecules are denatured into single-stranded molecules. The ends of the molecules are brought together by hybridization to a template. The template ensures that the two single-stranded nucleic acid molecules are aligned correctly. DNA ligase joins the two nucleic acid molecules into a single, larger, composite nucleic acid molecule. The nucleic acid molecules are subsequently denatured so that the composite molecule formed by the ligated nucleic acid molecules and the template cease to hybridize to each. Each composite molecule then serves as a template for orienting unligated, single-stranded nucleic acid molecules. After several cycles, composite nucleic acid molecules are generated from smaller nucleic acid molecules. A number of applications are disclosed for chain reaction cloning including site-specific ligation of DNA fragments generated by restriction enzyme digestion, DNAse digestion, chemical cleavage, enzymatic or chemical synthesis, and PCR amplification.

Figure 1C:
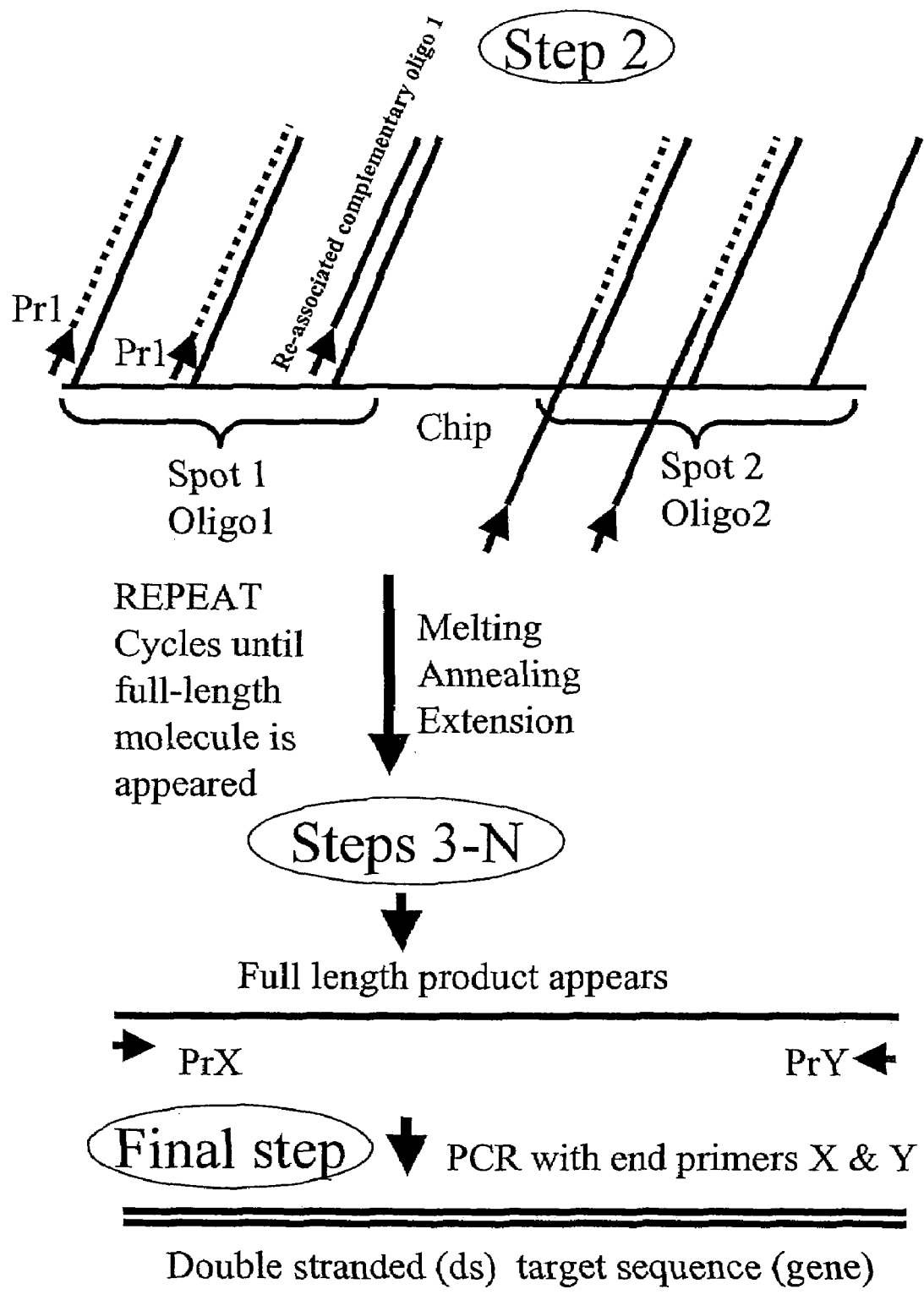
FIG. 1C shows a continuation of the assembly process from FIG. 1B. Specifically, step 3 of the process (i.e., melting, re-annealing and extension) leads to the same products as step 2 plus a product complementary to oligonucleotides 1+2+3. Cycles (steps) are repeated until a full-length complementary polynucleotide is formed. The final step is preparation of the final target polynucleotide molecule in desirable amounts by amplification (i.e., PCR) using two primers complementary to the ends of this molecule (PrX and PrY).

With regard to the second embodiment of the inventive process (illustrated in FIG. 2), a target polynucleotide gene sequence (either strand) is divided into number of overlapping oligonucleotide sequences by hand or with a software program, as shown in FIG. 1. These oligonucleotide sequences, plus flanking sequences A and B (having one or a plurality of restriction enzyme sites in the flanking region sequence), are synthesized (in situ) on microarray device, or on a bead solid surface using standard in situ synthesis techniques, or spotted (pre-synthesized) onto a microarray device using standard oligonucleotide synthesis procedures with standard spotting (e.g., computer-aided or ink jet printing) techniques. The oligonucleotide sequences are amplified, preferably using a PCR process with a pair of primers (Pr1 and Pr2). The primers are optionally labeled with specific binding moieties, such as biotin. The resulting amplified mixture of different amplified oligonucleotide sequences are double stranded (ds). The mixture of ds oligonucleotide sequences are treated with an appropriate restriction enzyme, such as an REII restriction enzyme (e.g., Mly I enzyme), to produce mixture of different double stranded (ds) overlapping oligonucleotide sequences that can be assembled into the structure of the desired polynucleotide (gene) and ds flanking sequences. Optionally, the flanking sequences and residual primers are removed from the ds oligonucleotide sequence mixture, preferably by a process of specific absorption using specific binding moieties introduced in the primers (e.g., biotin), or by a process of size fractionation based on the size differences of the specific oligonucleotide sequences and flanking sequences. The mixture of specific oligonucleotide sequences is assembled, for example, by a process of repeated cycles of melting, self-annealing and polymerase extension followed by PCR amplification of the final molecule with appropriate PCR primers designed to amplify this complete molecule (e.g., as described in Mullis et al., *Cold Spring Harb. Symp. Quant. Biol.* 51 Pt 1:263-73, 1986; and Saiki et al., *Science* 239:487-91, 1988).

In yet another embodiment of the inventive process (illustrated in FIG. 3), the oligonucleotide sequences comprising the target polynucleotide sequence are synthesized on a microarray device or bead solid support, each oligonucleotide having a cleavable linker moiety synthesized within the sequence, such that after synthesis, oligonucleotides can be cleaved from the microarray device into a solution. Examples of appropriate cleavable linker moieties are shown in FIG. 3A. In addition to this method of cleavage, a sequence containing RE enzyme site can be synthesized at the ends of oligonucleotides attached to the microarray device. These oligonucleotides on the microarray device then hybridize with an oligonucleotide complementary to this additional flanking sequence and treated with an RE enzyme specific for the RE enzyme site. This process releases oligonucleotide fragments resembling the structure of the target polynucleotide. This set of oligonucleotides then can be assembled into the final polynucleotide molecule using any one of the methods or combination of the methods of ligation, primer extension and PCR.

In a third embodiment of the inventive process, a plurality of oligonucleotides that can be assembled into a full length polynucleotide are synthesized on a microarray device (or beads having a solid surface) having specific cleavable linker moieties (FIG. 3A) or capable of being cleaved from the solid support of the microarray device or beads by a chemical treatment. The net effect is to recreate the functional 3' ends and 5' ends of each specific oligonucleotide sequence. After treatment to cleave them, the oligonucleotides (each having overlapping regions) are released into a mixture and used for full-length polynucleotide gene assembly using any of the gene assembly processes described herein.

Specifically, in the third embodiment and as illustrated in FIG. 3, a target polynucleotide sequence is dissected into number of overlapping oligonucleotide sequences by a software program or on paper, but not necessarily physically in a laboratory. These oligonucleotide sequences are physically synthesized on a microarray device. In alternative A, the oligonucleotide sequences are connected to the microarray device through cleavable linker moiety. Chemical cleavage under basic conditions (e.g., through addition of ammonia), at cleavable linker CL recreates the usual 3' end of the specific oligonucleotide sequences 1 through N. Oligonucleotide sequences 1 through N are released into a mixture. The mixture of oligonucleotide sequences is used for polynucleotide assembly.

In alternative B, oligonucleotide sequences are connected to a microarray device through additional flanking sequence regions containing a restriction enzyme (RE) sequence site. A second oligonucleotide fragment, complementary to the flanking sequence, is hybridized to the oligonucleotides on the microarray device. This recreates a ds structure at the flanking sequence region, including the RE recognition site. Digestion of this ds DNA structure with RE enzyme specific to the RE recognition site in the flanking sequence region will release specific oligonucleotides 1 through N into a mixture solution. The oligonucleotides 1 through N are able to assemble into a polynucleotide molecule in solution.

In another example of alternative B, oligonucleotides that together assemble into the polynucleotide are synthesized on a microarray device, each having a flanking sequence on the microarray side. The flanking sequence further comprises a restriction endonuclease (RE) recognition site (see FIG. 3B). Oligonucleotides complementary to the flanking sequence region are added and hybridized to the oligonucleotides on microarray device. After hybridization a RE (restriction enzyme specific to the RE sequence in the flanking region) is added to the microarray device. Specific oligonucleotide sequences are released from the microarray device as a result of RE digestion into a mixture. The mixture of specific oligonucleotide sequences assembled into the full-length polynucleotide sequence.

EXAMPLE 1

This example illustrates assembly of 172-mer polynucleotide sequence from non-cleavable oligonucleotide sequences synthesized on a microarray device according to the first embodiment inventive process (FIGS. 4 and 5). Three oligonucleotides (sequences shown in FIG. 5) were synthesized in situ on a microarray device according to an electrochemical process (see U.S. Pat. No. 6,093,302, the disclosure of which is incorporated by reference herein). The oligonucleotide sequences synthesized were amplified by a PCR reaction with primers X (complementary to the strand of oligo#1) and Z (same strand as oligo#3) (FIG. 5). After 45 cycles of PCR using a PCR kit with AmplyGold® enzyme (Applied Biosystems) a correct DNA fragment of 172 bp was synthesized (FIG. 4). Its subsequent digestion confirmed the specificity of this enzyme with HpaII producing two fragments of 106 bp and 68 bp.

EXAMPLE 2

This example illustrates the second embodiment of the inventive process for preparing oligonucleotides for assembly into full-length polynucleotides by PCR and REII (restriction enzyme) digestion. A single oligonucleotide sequence was synthesized on a microarray device according to the procedure in Example 1 (see FIGS. 2 and 6). The oligonucleotide sequence further comprised 2 flanking sequences, each having a recognition site for a MlyI restriction enzyme. This microarray device was subject to a PCR (25 cycles) reaction with two primers (shown in FIG. 7) to produce an amplified PCR fragment mixture. The amplified PCR fragment obtained was digested by MlyI restriction enzyme and purified by a PCR purification kit (Qiagen) to produce specific oligonucleotides ready for assembly (FIG. 7). Similarly, this specific oligonucleotide was purified from the flanking sequences by absorption of the digestion mixture by Streptavidin-agarose (Sigma).

EXAMPLE 3

This example illustrates the assembly of a 290 bp polynucleotide sequence from 9 oligonucleotide sequences, each having flanking sequences containing a MlyI restriction site. Each of the nine different oligonucleotide sequences was synthesized on a microarray device through an in situ electrochemistry process as described in example 1 herein.

Figure 6:
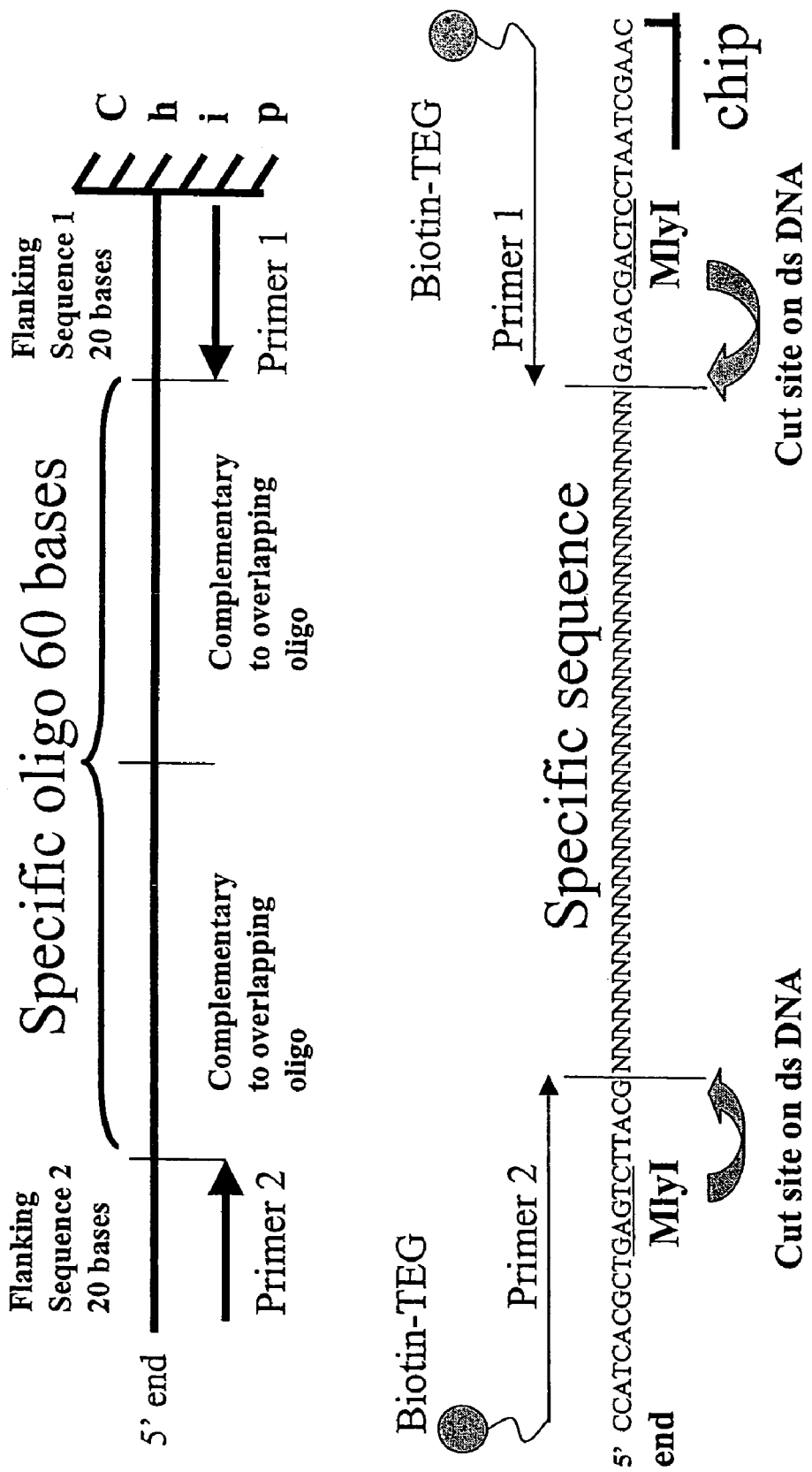
FIG. 6 shows a scheme for preparing the sequences of flanking regions and primers used for preparation of specific oligonucleotide for assembly using the REII enzyme MlyI. Primer 1 is complementary to the oligonucleotide strand on a microarray device and contains a Biotin-TEG (triethylene glycol) moiety. Primer 2 is the same strand as the oligonucleotide strand on microarray device and contains Biotin-TEG moiety. Any sequence between the primers can be used and is just designated by a string of N's.
Figure 7:
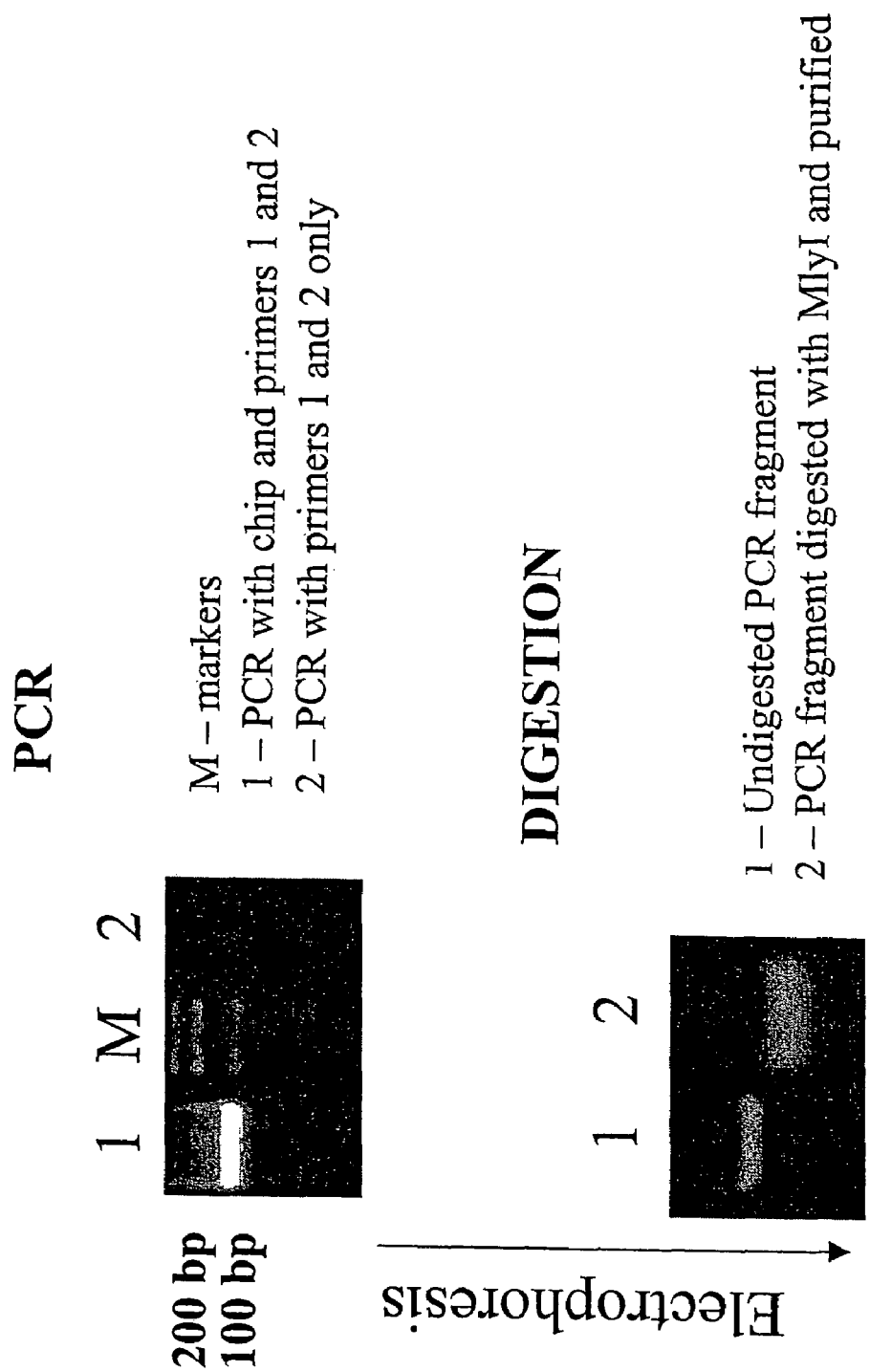
FIG. 7 shows the results of PCR and MlyI digestion of an oligonucleotide sequence as described in FIG. 6. The clean bands show the ability to obtain pure oligonucleotides using the second embodiment of the inventive process to cleave off oligonucleotide sequences using appropriate restriction enzymes.

The microarray device containing the nine specific oligonucleotide sequences (with flanking sequences as shown in FIG. 8) was used for PCR amplification of each oligonucleotide sequence using two primers, Primer 1 and 2, described in FIG. 6 to form a mixture of ds oligonucleotide sequences. The primers were complementary to the flanking sequences. The mixture of the amplified ds oligonucleotide sequences was digested by MlyI enzyme. Specific ds oligonucleotide sequences were purified and then assembled into the final 290 bp polynucleotide sequence in two steps as described in FIG. 2 and shown schematically in FIG. 9. At the first step of assembly 20 cycles of melting-annealing-extension were used. The final product was amplified using two primers FP1 and FP2 (FIG. 9) in 25 cycles of PCR into a 290 bp polynucleotide DNA.

EXAMPLE 4

This example illustrates the creation of a cDNA polynucleotide sequence capable of coding on expression for fusion protein MIP-GFP-FLAG (Macrophage Inflammation Protein—Green Fluorescence Protein—FLAG peptide) using thirty-eight overlapping oligonucleotide sequences (FIG. 10). The 38 oligonucleotides were synthesized on a microarray device using an electrochemical in situ synthesis approach, as described in example 1. Each oligonucleotide sequence contained a cleavable linker moiety (see FIG. 3A) at their 3' end. After simultaneous deprotection and cleavage of these oligonucleotide sequences by concentrated ammonia, the mixture of oligonucleotide sequences was purified by gel-filtration through the spin column. The purified oligonucleotide sequences were assembled into a polynucleotide by a process shown schematically in FIG. 3. The resulting DNA polynucleotide was 965 bp and contained both a T7 RNA-polymerase promoter and a coding sequence for MIP-GFP-FLAG fusion protein. The polynucleotide assembled in this example was used in a standard transcription/translation reaction and produced the appropriate MIP-GFP-FLAG fusion protein. The translated protein was purified from the reaction mixture using anti-FLAG resin (Sigma). The functional protein possessed green fluorescence signal in appropriate blue light. Accordingly, this experiment demonstrated that the inventive gene assembly process provided the correct DNA sequence coding for the functional protein.

I claim:

1. A process for assembling a polynucleotide from a plurality of different oligonucleotides comprising:
   (a) providing the plurality of different oligonucleotides that together comprise the polynucleotide sequence, wherein each of said oligonucleotides has an overlapping sequence region corresponding to a sequence region in a next oligonucleotide, and wherein a plurality of the different oligonucleotides further comprises flanking sequence regions at the 3' and 5' ends thereof, wherein said flanking sequence regions comprise primer binding sites that are the same for each oligonucleotide and a sequence segment having a restriction enzyme recognition sequence for removing the primer binding sites;
   (b) amplifying each oligonucleotide using a pair of primers complementary to the primer binding sites of the flanking sequence regions;
   (c) cleaving the oligonucleotides to remove the primer binding sites; and
   (d) assembling the cleaved oligonucleotides through the overlapping sequence regions to form a full length polynucleotide.

2. The process of claim 1 further comprising, prior to step (a), synthesizing in situ or spotting the plurality of different oligonucleotides on a microarray device or bead device each having a solid or porous surface, wherein the plurality of different oligonucleotides are attached to the solid or porous surface.

3. The process of claim 2 wherein each oligonucleotide is attached to the solid or porous surface through a cleavable linker moiety.

4. The process of claim 3 further comprising cleaving the cleavable linker moiety to cleave each oligonucleotide from the microarray or bead solid surface to form a soluble mixture of oligonucleotides.

5. The process of claim 4 wherein the cleavable linker is a chemical composition having a succinate moiety bound to a nucleotide moiety such that cleavage produces a 3' hydroxy nucleotide.

6. The process of claim 5 wherein the cleavable linker is selected from the group consisting of 5'-dimethoxytrityl-thymidine-3'-succinate, 4-N-benzoyl-5'-dimethoxytrityl-deoxycytidine-3'-succinate, 1-N-benzoyl-5'-dimethoxytrityl-deoxyadenosine-3'-succinate, 2-N-isobutyryl-5'-dimethoxytrityl-deoxyguanosone-3'-succinate, and combinations thereof.

7. The process of claim 2 wherein the flanking sequence region at an end attached to the solid or porous surface comprises a sequence segment having a restriction enzyme recognition sequence capable of being cleaved by a corresponding restriction enzyme.

8. The process of claim 7 further comprising hybridizing an oligonucleotide complementary to the flanking sequence region at an end attached to the solid or porous surface to form a double stranded sequence capable of interacting with the corresponding restriction enzyme and digesting the oligonucleotides to cleave them from the microarray device or beads to form a soluble mixture of oligonucleotides.

9. The process of claim 1 wherein the flanking sequence regions are from about 7 to about 50 bases in length.

10. The process of claim 1 wherein the restriction enzyme recognition sequence is a class II endonuclease restriction site sequence capable of being cleaved by its corresponding class II restriction endonuclease enzyme.

11. The process of claim 10 wherein the restriction endonuclease class II site corresponds to restriction sites for a restriction endonuclease class II enzyme selected from the group consisting of Mly I, BspM I, BaeI, BsaX I, BsrI, Bmr I, Btr I, BtsI, FokI, and combinations thereof.

12. The process of claim 1 wherein the flanking sequence regions further comprise a binding moiety used to purify cleaved oligonucleotides from flanking sequences.

13. The process of claim 12 wherein the process further comprises the step of labeling the flanking sequence regions during the amplification step (b) using primer sequences labeled with binding moieties.

14. The process of claim 13 wherein the binding moiety is biotin or fluorescein.

15. The process of claim 1 wherein the flanking sequence regions for each oligonucleotide are the same.

16. The process of claim 1 wherein the primer binding sites for each oligonucleotide are the same.

17. The process of claim 1 wherein the process further comprises amplifying the full length polynucleotide sequence using primers complementary to the ends thereof.

18. The process of claim 1 wherein the flanking sequence regions are designed to have minimal homology to the oligonucleotide sequences.

19. The process of claim 1 wherein assembly comprises repeated cycles of melting, self-annealing and polymerase extension.

20. The process of claim 1 wherein cleaved oligonucleotides are purified from flanking sequence regions based on size.

21. The method of claim 1 wherein each oligonucleotide has a sequence region complementary to a sequence region in a next oligonucleotide that permits formation of an overlap suitable for primer extension by polymerase.

22. The method of claim 1 wherein each oligonucleotide has a sequence region of five or more bases that is complementary to a sequence region in a next oligonucleotide.

23. The method of claim 1 wherein each oligonucleotide has a sequence region of 15-25 bases that is complementary to a sequence region in a next oligonucleotide.

* * * * *

SEQUENCE LISTING

<160> NUMBER OF SEQ ID NOS: 51

<210> SEQ ID NO 1
<211> LENGTH: 82
<212> TYPE: DNA
<213> ORGANISM: Artificial Sequence
<220> FEATURE:
<223> OTHER INFORMATION: Primer X #1 Figure 5

<400> SEQUENCE: 1
taattatgct gagtgatatc cctttctacc tgtgcggctg gcggacgacg aagtcgaatg      60
tggagggccg tctaaggtgt ct                                              82

<210> SEQ ID NO 2
<211> LENGTH: 84
<212> TYPE: DNA
<213> ORGANISM: Artificial Sequence
<220> FEATURE:
<223> OTHER INFORMATION: Primer X #2 Figure 5

<400> SEQUENCE: 2
ggacgacgaa gtcgaatgtg gagggccgtc taaggtgtct taaagtatcg actgatgaaa      60
ctctgctcgt cggtcacgag gttc                                            84

<210> SEQ ID NO 3
<211> LENGTH: 86
<212> TYPE: DNA
<213> ORGANISM: Artificial Sequence
<220> FEATURE:
<223> OTHER INFORMATION: Primer Z #3 Figure 5

<400> SEQUENCE: 3
gtatcgactg atgaaactct gctcgtcggt cacgaggttc cctcgaccac cgcatgatgt      60
ttctgctact gctgttcacg attatc                                          86

<210> SEQ ID NO 4
<211> LENGTH: 172
<212> TYPE: DNA
<213> ORGANISM: Artificial Sequence
<220> FEATURE:
<223> OTHER INFORMATION: Final assembled product Figure 5

<400> SEQUENCE: 4
taattatgct gagtgatatc cctttctacc tgtgcggctg gcggacgacg aagtcgaatg      60
tggagggccg tctaaggtgt cttaaagtat cgactgatga aactctgctc gtcggtcacg     120
aggttccctc gaccaccgca tgatgtttct gctactgctg ttcacgatta tc             172

<210> SEQ ID NO 5
<211> LENGTH: 89
<212> TYPE: DNA
<213> ORGANISM: Artificial Sequence
<220> FEATURE:
<223> OTHER INFORMATION: Fragment #1 Figure 8

<400> SEQUENCE: 5

-continued ccatcacgct gagtcttacg tacgtaatac gactcactat agggaaagtc gccaccatgg    60
acacgccgac gagacgactc ctaatcgaa                                       89

<210> SEQ ID NO 6
<211> LENGTH: 85
<212> TYPE: DNA
<213> ORGANISM: Artificial Sequence
<220> FEATURE:
<223> OTHER INFORMATION: Fragment #2 Figure 8

<400> SEQUENCE: 6
ccatcacgct gagtcttacg cgcctgctgc ttcagctaca cctcccggca gattccacag    60
aatttcgaga cgactcctaa tcgaa                                           85

<210> SEQ ID NO 7
<211> LENGTH: 87
<212> TYPE: DNA
<213> ORGANISM: Artificial Sequence
<220> FEATURE:
<223> OTHER INFORMATION: Fragment #3 Figure 8

<400> SEQUENCE: 7
ccatcacgct gagtcttacg atagctgact actttgagac gagcagccag tgctccaagc    60
ccggtgtcga gacgactcct aatcgaa                                         87

<210> SEQ ID NO 8
<211> LENGTH: 81
<212> TYPE: DNA
<213> ORGANISM: Artificial Sequence
<220> FEATURE:
<223> OTHER INFORMATION: Fragment #4 Figure 8

<400> SEQUENCE: 8
ccatcacgct gagtcttacg atcttcctaa ccaagcgaag ccggcaggtc tgtgctgacc    60
ccgagacgac tcctaatcga a                                               81

<210> SEQ ID NO 9
<211> LENGTH: 130
<212> TYPE: DNA
<213> ORGANISM: Artificial Sequence
<220> FEATURE:
<223> OTHER INFORMATION: Fragment #5 Figure 8

<400> SEQUENCE: 9
ccatcacgct gagtcttacg caggcactca gctctacggg gccgtcgccg atgggggtgt    60
tctgctggta gtggtcggcg agctgcatat ttctggaccc actcctcact gagacgactc   120
ctaatcgaac                                                           130

<210> SEQ ID NO 10
<211> LENGTH: 83
<212> TYPE: DNA
<213> ORGANISM: Artificial Sequence
<220> FEATURE:
<223> OTHER INFORMATION: Fragment #6 Figure 8

<400> SEQUENCE: 10
ccatcacgct gagtcttacg atatttctgg acccactcct cactgggtc agcacagacc     60 tgccgagacg actcctaatc gaa                                             83

<210> SEQ ID NO 11
<211> LENGTH: 84

```
<212> TYPE: DNA
<213> ORGANISM: Artificial Sequence
<220> FEATURE:
<223> OTHER INFORMATION: Fragment #7 Figure 8

<400> SEQUENCE: 11
ccatcacgct gagtcttacg ggcttcgctt ggttaggaag atgacaccgg gcttggagca    60
ctggcgagac gactcctaat cgaa                                          84

<210> SEQ ID NO 12
<211> LENGTH: 84
<212> TYPE: DNA
<213> ORGANISM: Artificial Sequence
<220> FEATURE:
<223> OTHER INFORMATION: Fragment #8 Figure 8

<400> SEQUENCE: 12
ccatcacgct gagtcttacg tgctcgtctc aaagtagtca gctatgaaat tctgtggaat    60
ctgccgagac gactcctaat cgaa                                          84

<210> SEQ ID NO 13
<211> LENGTH: 88
<212> TYPE: DNA
<213> ORGANISM: Artificial Sequence
<220> FEATURE:
<223> OTHER INFORMATION: Fragment #9 Figure 8

<400> SEQUENCE: 13
ccatcacgct gagtcttacg gggaggtgta gctgaagcag caggcggtcg gcgtgtccat    60
ggtggcgacg agacgactcc taatcgaa                                      88

<210> SEQ ID NO 14
<211> LENGTH: 50
<212> TYPE: DNA
<213> ORGANISM: Artificial Sequence
<220> FEATURE:
<223> OTHER INFORMATION: Fragment #1 Figure 10

<400> SEQUENCE: 14
tacgtaatac gactcactat agggaaagtc gccaccatgg acacgccgac                50

<210> SEQ ID NO 15
<211> LENGTH: 46
<212> TYPE: DNA
<213> ORGANISM: Artificial Sequence
<220> FEATURE:
<223> OTHER INFORMATION: Fragment #2 Figure 10

<400> SEQUENCE: 15
cgcctgctgc ttcagctaca cctcccggca gattccacag aatttc                    46

<210> SEQ ID NO 16
<211> LENGTH: 48
<212> TYPE: DNA
<213> ORGANISM: Artificial Sequence
<220> FEATURE:
<223> OTHER INFORMATION: Fragment #3 Figure 10

<400> SEQUENCE: 16
atagctgact actttgagac gagcagccag tgctccaagc ccggtgtc                 48

<210> SEQ ID NO 17
<211> LENGTH: 42
<212> TYPE: DNA
```

```
<213> ORGANISM: Artificial Sequence
<220> FEATURE:
<223> OTHER INFORMATION: Fragment #4 Figure 10

<400> SEQUENCE: 17
atcttcctaa ccaagcgaag ccggcaggtc tgtgctgacc cc                              42

<210> SEQ ID NO 18
<211> LENGTH: 47
<212> TYPE: DNA
<213> ORGANISM: Artificial Sequence
<220> FEATURE:
<223> OTHER INFORMATION: Fragment #5 Figure 10

<400> SEQUENCE: 18
agtgaggagt gggtccagaa atatgtcagc gacctagagc tgagtgc                        47

<210> SEQ ID NO 19
<211> LENGTH: 44
<212> TYPE: DNA
<213> ORGANISM: Artificial Sequence
<220> FEATURE:
<223> OTHER INFORMATION: Fragment #6 Figure 10

<400> SEQUENCE: 19
atatttctgg acccactcct cactggggtc agcacagacc tgcc                           44

<210> SEQ ID NO 20
<211> LENGTH: 45
<212> TYPE: DNA
<213> ORGANISM: Artificial Sequence
<220> FEATURE:
<223> OTHER INFORMATION: Fragment #7 Figure 10

<400> SEQUENCE: 20
ggcttcgctt ggttaggaag atgacaccgg gcttggagca ctggc                          45

<210> SEQ ID NO 21
<211> LENGTH: 45
<212> TYPE: DNA
<213> ORGANISM: Artificial Sequence
<220> FEATURE:
<223> OTHER INFORMATION: Fragment #8 Figure 10

<400> SEQUENCE: 21
tgctcgtctc aaagtagtca gctatgaaat tctgtggaat ctgcc                          45

<210> SEQ ID NO 22
<211> LENGTH: 49
<212> TYPE: DNA
<213> ORGANISM: Artificial Sequence
<220> FEATURE:
<223> OTHER INFORMATION: Fragment #9 Figure 10

<400> SEQUENCE: 22
gggaggtgta gctgaagcag caggcggtcg gcgtgtccat ggtggcgac                      49

<210> SEQ ID NO 23
<211> LENGTH: 54
<212> TYPE: DNA
<213> ORGANISM: Artificial Sequence
<220> FEATURE:
<223> OTHER INFORMATION: Fragment #1F Figure 10

<400> SEQUENCE: 23
ggtgaacagc tcctcgccct tgctcaccat ggcactcagc tctaggtcgc tgac                54
```

<210> SEQ ID NO 24
<211> LENGTH: 52
<212> TYPE: DNA
<213> ORGANISM: Artificial Sequence
<220> FEATURE:
<223> OTHER INFORMATION: Fragment #2F Figure 10

<400> SEQUENCE: 24
catggtgagc aagggcgagg agctgttcac cggggtggtg cccatcctgg tc        52

<210> SEQ ID NO 25
<211> LENGTH: 50
<212> TYPE: DNA
<213> ORGANISM: Artificial Sequence
<220> FEATURE:
<223> OTHER INFORMATION: Fragment #3F Figure 10

<400> SEQUENCE: 25
ttgtggccgt ttacgtcgcc gtccagctcg accaggatgg gcaccacccc        50

<210> SEQ ID NO 26
<211> LENGTH: 51
<212> TYPE: DNA
<213> ORGANISM: Artificial Sequence
<220> FEATURE:
<223> OTHER INFORMATION: Fragment #4F Figure 10

<400> SEQUENCE: 26
gagctggacg gcgacgtaaa cggccacaag ttcagcgtgt ccggcgaggg c        51

<210> SEQ ID NO 27
<211> LENGTH: 45
<212> TYPE: DNA
<213> ORGANISM: Artificial Sequence
<220> FEATURE:
<223> OTHER INFORMATION: Fragment #5F Figure 10

<400> SEQUENCE: 27
ttgccgtagg tggcatcgcc ctcgccctcg ccggacacgc tgaac        45

<210> SEQ ID NO 28
<211> LENGTH: 48
<212> TYPE: DNA
<213> ORGANISM: Artificial Sequence
<220> FEATURE:
<223> OTHER INFORMATION: Fragment #6F Figure 10

<400> SEQUENCE: 28
gagggcgatg ccacctacgg caagctgacc ctgaagttca tctgcacc        48

<210> SEQ ID NO 29
<211> LENGTH: 48
<212> TYPE: DNA
<213> ORGANISM: Artificial Sequence
<220> FEATURE:
<223> OTHER INFORMATION: Fragment #7F Figure 10

<400> SEQUENCE: 29
cagggcacgg gcagcttgcc ggtggtgcag atgaacttca gggtcagc        48

<210> SEQ ID NO 30
<211> LENGTH: 54
<212> TYPE: DNA
<213> ORGANISM: Artificial Sequence
<220> FEATURE:

```
<223> OTHER INFORMATION: Fragment #8F Figure 10

<400> SEQUENCE: 30
accggcaagc tgcccgtgcc ctggcccacc ctcgtgacca ccctgaccta cggc            54

<210> SEQ ID NO 31
<211> LENGTH: 55
<212> TYPE: DNA
<213> ORGANISM: Artificial Sequence
<220> FEATURE:
<223> OTHER INFORMATION: Fragment #9F Figure 10

<400> SEQUENCE: 31
ggggtagcgg ctgaagcact gcacgccgta ggtcagggtg gtcacgaggg tgggc           55

<210> SEQ ID NO 32
<211> LENGTH: 48
<212> TYPE: DNA
<213> ORGANISM: Artificial Sequence
<220> FEATURE:
<223> OTHER INFORMATION: Fragment #10F Figure 10

<400> SEQUENCE: 32
gtgcagtgct tcagccgcta ccccgaccac atgaagcagc acgacttc                  48

<210> SEQ ID NO 33
<211> LENGTH: 51
<212> TYPE: DNA
<213> ORGANISM: Artificial Sequence
<220> FEATURE:
<223> OTHER INFORMATION: Fragment #11F Figure 10

<400> SEQUENCE: 33
gtagccttcg ggcatggcgg acttgaagaa gtcgtgctgc ttcatgtggt c               51

<210> SEQ ID NO 34
<211> LENGTH: 51
<212> TYPE: DNA
<213> ORGANISM: Artificial Sequence
<220> FEATURE:
<223> OTHER INFORMATION: Fragment #12F Figure 10

<400> SEQUENCE: 34
ttcaagtccg ccatgcccga aggctacgtc caggagcgca ccatcttctt c               51

<210> SEQ ID NO 35
<211> LENGTH: 49
<212> TYPE: DNA
<213> ORGANISM: Artificial Sequence
<220> FEATURE:
<223> OTHER INFORMATION: Fragment #13F Figure 10

<400> SEQUENCE: 35
gggtcttgta gttgccgtcg tccttgaaga agatggtgcg ctcctggac                 49

<210> SEQ ID NO 36
<211> LENGTH: 48
<212> TYPE: DNA
<213> ORGANISM: Artificial Sequence
<220> FEATURE:
<223> OTHER INFORMATION: Fragment #14F Figure 10

<400> SEQUENCE: 36
aaggacgacg gcaactacaa gacccgcgcc gaggtgaagt tcgagggc                  48
```

```
<210> SEQ ID NO 37
<211> LENGTH: 49
<212> TYPE: DNA
<213> ORGANISM: Artificial Sequence
<220> FEATURE:
<223> OTHER INFORMATION: Fragment #15F Figure 10

<400> SEQUENCE: 37
agctcgatgc ggttcaccag ggtgtcgccc tcgaacttca cctcggcgc         49

<210> SEQ ID NO 38
<211> LENGTH: 51
<212> TYPE: DNA
<213> ORGANISM: Artificial Sequence
<220> FEATURE:
<223> OTHER INFORMATION: Fragment #16F Figure 10

<400> SEQUENCE: 38
gacaccctgg tgaaccgcat cgagctgaag ggcatcgact caaggagga c        51

<210> SEQ ID NO 39
<211> LENGTH: 51
<212> TYPE: DNA
<213> ORGANISM: Artificial Sequence
<220> FEATURE:
<223> OTHER INFORMATION: Fragment #17F Figure 10

<400> SEQUENCE: 39
tccagcttgt gccccaggat gttgccgtcc tccttgaagt cgatgccctt c        51

<210> SEQ ID NO 40
<211> LENGTH: 51
<212> TYPE: DNA
<213> ORGANISM: Artificial Sequence
<220> FEATURE:
<223> OTHER INFORMATION: Fragment #18F Figure 10

<400> SEQUENCE: 40
ggcaacatcc tggggcacaa gctggagtac aactacaaca gccacaacgt c        51

<210> SEQ ID NO 41
<211> LENGTH: 52
<212> TYPE: DNA
<213> ORGANISM: Artificial Sequence
<220> FEATURE:
<223> OTHER INFORMATION: Fragment #19F Figure 10

<400> SEQUENCE: 41
gttcttctgc ttgtcggcca tgatatagac gttgtggctg ttgtagttgt ac       52

<210> SEQ ID NO 42
<211> LENGTH: 51
<212> TYPE: DNA
<213> ORGANISM: Artificial Sequence
<220> FEATURE:
<223> OTHER INFORMATION: Fragment #20F Figure 10

<400> SEQUENCE: 42
tatatcatgg ccgacaagca gaagaacggc atcaaggtga acttcaagat c        51

<210> SEQ ID NO 43
<211> LENGTH: 50
<212> TYPE: DNA
<213> ORGANISM: Artificial Sequence
<220> FEATURE:
<223> OTHER INFORMATION: Fragment #21F Figure 10
```

-continued

<400> SEQUENCE: 43
acgctgccgt cctcgatgtt gtggcggatc ttgaagttca ccttgatgcc                50

<210> SEQ ID NO 44
<211> LENGTH: 49
<212> TYPE: DNA
<213> ORGANISM: Artificial Sequence
<220> FEATURE:
<223> OTHER INFORMATION: Fragment #22F Figure 10

<400> SEQUENCE: 44
cgccacaaca tcgaggacgg cagcgtgcag ctcgccgacc actaccagc                49

<210> SEQ ID NO 45
<211> LENGTH: 51
<212> TYPE: DNA
<213> ORGANISM: Artificial Sequence
<220> FEATURE:
<223> OTHER INFORMATION: Fragment #23F Figure 10

<400> SEQUENCE: 45
acggggccgt cgccgatggg ggtgttctgc tggtagtggt cggcgagctg c              51

<210> SEQ ID NO 46
<211> LENGTH: 51
<212> TYPE: DNA
<213> ORGANISM: Artificial Sequence
<220> FEATURE:
<223> OTHER INFORMATION: Fragment #24F Figure 10

<400> SEQUENCE: 46
agaacacccc catcggcgac ggccccgtgc tgctgcccga caaccactac c              51

<210> SEQ ID NO 47
<211> LENGTH: 49
<212> TYPE: DNA
<213> ORGANISM: Artificial Sequence
<220> FEATURE:
<223> OTHER INFORMATION: Fragment #25F Figure 10

<400> SEQUENCE: 47
tttgctcagg gcggactggg tgctcaggta gtggttgtcg ggcagcagc                49

<210> SEQ ID NO 48
<211> LENGTH: 50
<212> TYPE: DNA
<213> ORGANISM: Artificial Sequence
<220> FEATURE:
<223> OTHER INFORMATION: Fragment #26F Figure 10

<400> SEQUENCE: 48
tgagcaccca gtccgccctg agcaaagacc ccaacgagaa gcgcgatcac                50

<210> SEQ ID NO 49
<211> LENGTH: 51
<212> TYPE: DNA
<213> ORGANISM: Artificial Sequence
<220> FEATURE:
<223> OTHER INFORMATION: Fragment #27F Figure 10

<400> SEQUENCE: 49
ggcggtcacg aactccagca ggaccatgtg atcgcgcttc tcgttggggt c              51

<210> SEQ ID NO 50
<211> LENGTH: 51

-continued

```
<212> TYPE: DNA
<213> ORGANISM: Artificial Sequence
<220> FEATURE:
<223> OTHER INFORMATION: Fragment #28F Figure 10

<400> SEQUENCE: 50
atggtcctgc tggagttcgt gaccgccgcc gggatcactc tcggcatgga c            51

<210> SEQ ID NO 51
<211> LENGTH: 49
<212> TYPE: DNA
<213> ORGANISM: Artificial Sequence
<220> FEATURE:
<223> OTHER INFORMATION: Fragment #29F Figure 10

<400> SEQUENCE: 51
ggcggccgct ttacttgtac agctcgtcca tgccgagagt gatcccggc               49
```